US 8,979,785 B2

(12) United States Patent
Korogi et al.

(10) Patent No.: US 8,979,785 B2
(45) Date of Patent: Mar. 17, 2015

(54) FLUID APPLICATION DEVICE AND METHOD

(75) Inventors: Todd M. Korogi, Raleigh, NC (US); Theodore J. Mosler, Raleigh, NC (US); Matthew R. Penny, Cary, NC (US); Bryan J. Peters, Raleigh, NC (US); Lisa D. Shaffer, Raleigh, NC (US); Andrew Corson, Apex, NC (US); Ronald J. Casey, Silver Spring, MD (US); Patrick P. Vanek, Frederick, MD (US); Royal D. Hathaway, Montgomery Village, MD (US)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 1129 days.

(21) Appl. No.: 12/654,664

(22) Filed: Dec. 29, 2009

(65) Prior Publication Data
US 2010/0168638 A1 Jul. 1, 2010

Related U.S. Application Data

(60) Provisional application No. 61/141,544, filed on Dec. 30, 2008.

(51) Int. Cl.
*A61M 35/00* (2006.01)
*A61F 13/40* (2006.01)

(52) U.S. Cl.
CPC .................................. *A61M 35/006* (2013.01)
USPC ....... 604/3; 604/2; 604/19; 604/289; 604/290

(58) Field of Classification Search
CPC ............ B43K 5/14; B43K 5/00; B65D 47/42; B65D 47/00; A61M 35/006; A61M 35/00; A61M 35/003; A45D 34/04; A45D 2200/1018; B05C 17/002
USPC ............... 604/2–3, 1, 19, 289–290, 317, 319, 604/540, 543, 544; 222/1; 401/133, 261
See application file for complete search history.

(56) References Cited

U.S. PATENT DOCUMENTS 1,715,914 A 6/1929 Halk
2,180,248 A 11/1939 Layne
(Continued)

FOREIGN PATENT DOCUMENTS

CA 1284784 6/1991
CN 2280607 Y 5/1998
(Continued)

OTHER PUBLICATIONS

International Search Report re PCT/US2009/069733, Mar. 26, 2010.
(Continued)

*Primary Examiner* — Tatyana Zalukaeva
*Assistant Examiner* — Benedict L Hanrahan
(74) *Attorney, Agent, or Firm* — Finnegan, Henderson, Farabow, Garrett & Dunner LLP

(57) ABSTRACT

An applicator device for applying a fluid is provided. The applicator device may include a handle. The handle may comprise an elongate hollow body having a proximal end and a distal end and at least one longitudinal, interior rib disposed on an inner surface of an outer wall of the hollow body and configured to orient and guide a container for containing the fluid when the container is disposed within the hollow body. In addition, the applicator device may include a base at the distal end of the hollow body. Further, the applicator device may include an applicator pad coupled to the base.

43 Claims, 20 Drawing Sheets

(56) References Cited

U.S. PATENT DOCUMENTS

| | | | |
|---|---|---|---|
| 2,218,862 A | 10/1940 | Vredenburgh | |
| 2,568,328 A | 9/1951 | Elby | |
| 2,783,489 A | 3/1957 | Bogoslowsky | |
| 3,386,793 A | 6/1968 | Stanton | |
| 3,613,685 A | 10/1971 | Reynolds | |
| 3,647,305 A | 3/1972 | Baker et al. | |
| 3,647,605 A | 3/1972 | Spiegel | |
| 3,687,140 A | 8/1972 | Reynolds | |
| 3,757,782 A | 9/1973 | Aiken | |
| 3,774,609 A | 11/1973 | Schwartzman | |
| 3,826,259 A | 7/1974 | Bailey | |
| 3,891,331 A | 6/1975 | Avery | |
| 3,901,233 A | 8/1975 | Grossan | |
| 3,929,135 A | 12/1975 | Thompson | |
| D245,221 S | 8/1977 | Hoyt | |
| 4,127,339 A | 11/1978 | Malacheski et al. | |
| 4,148,318 A | 4/1979 | Meyer | |
| 4,183,684 A | 1/1980 | Avery, Jr. | |
| 4,219,283 A | 8/1980 | Buckley et al. | |
| 4,291,697 A | 9/1981 | Georgevich | |
| 4,304,869 A * | 12/1981 | Dyke | 435/287.6 |
| 4,427,115 A | 1/1984 | Laipply | |
| 4,430,013 A | 2/1984 | Kaufman | |
| 4,519,795 A | 5/1985 | Hitchcock, Jr. et al. | |
| 4,594,835 A | 6/1986 | Gray | |
| 4,643,725 A | 2/1987 | Schlesser et al. | |
| D288,780 S | 3/1987 | Miller | |
| 4,648,506 A | 3/1987 | Campbell | |
| 4,696,393 A | 9/1987 | Laipply | |
| 4,701,168 A | 10/1987 | Gammons | |
| D292,672 S | 11/1987 | Duell | |
| 4,812,067 A | 3/1989 | Brown et al. | |
| 4,869,612 A | 9/1989 | Mooney et al. | |
| 4,875,602 A | 10/1989 | Chickering et al. | |
| 4,896,768 A | 1/1990 | Anderson | |
| 4,921,137 A | 5/1990 | Heijenga | |
| 4,925,327 A | 5/1990 | Wirt | |
| 4,927,283 A | 5/1990 | Fitjer | |
| 4,957,385 A | 9/1990 | Weinstein | |
| 4,963,045 A | 10/1990 | Willcox | |
| 5,087,138 A | 2/1992 | Terbrusch et al. | |
| 5,098,297 A | 3/1992 | Chari et al. | |
| 5,135,112 A | 8/1992 | Kamen et al. | |
| 5,135,472 A | 8/1992 | Hermann et al. | |
| 5,181,621 A | 1/1993 | Plaehn | |
| 5,288,159 A | 2/1994 | Wirt | |
| 5,308,611 A | 5/1994 | Thompson | |
| D351,338 S | 10/1994 | Koptis | |
| 5,376,686 A | 12/1994 | Ishikawa et al. | |
| 5,435,660 A | 7/1995 | Wirt | |
| 5,489,280 A | 2/1996 | Russell | |
| 5,509,744 A | 4/1996 | Frazier | |
| 5,577,851 A | 11/1996 | Koptis | |
| 5,597,255 A | 1/1997 | Yager et al. | |
| 5,616,348 A | 4/1997 | Winicov | |
| 5,658,084 A | 8/1997 | Wirt | |
| D386,849 S | 11/1997 | Dehavilland | |
| 5,702,404 A | 12/1997 | Willingham | |
| 5,713,843 A | 2/1998 | Vangsness | |
| D396,126 S | 7/1998 | Ohmart | |
| 5,775,826 A | 7/1998 | Miller | |
| D396,911 S | 8/1998 | DeHavilland | |
| 5,791,801 A | 8/1998 | Miller | |
| 5,800,825 A | 9/1998 | McMullen | |
| 5,829,902 A | 11/1998 | Fomby | |
| 5,908,256 A | 6/1999 | Bernstein | |
| 5,916,882 A | 6/1999 | Jeng | |
| D416,389 S | 11/1999 | Frazier | |
| 6,019,765 A | 2/2000 | Thornhill et al. | |
| 6,039,488 A | 3/2000 | Krawczyk et al. | |
| 6,126,633 A | 10/2000 | Kaji et al. | |
| D434,525 S | 11/2000 | Angeletta | |
| 6,155,990 A | 12/2000 | Fournier | |
| 6,248,085 B1 * | 6/2001 | Scholz et al. | 604/2 |
| D448,521 S | 9/2001 | Angeletta | |
| 6,315,480 B1 | 11/2001 | Martel et al. | |
| 6,371,675 B1 | 4/2002 | Hoang et al. | |
| 6,415,470 B1 | 7/2002 | Ramrattan | |
| 6,419,642 B1 | 7/2002 | Marchitto et al. | |
| 6,422,778 B2 | 7/2002 | Baumann et al. | |
| D461,596 S | 8/2002 | Angeletta | |
| D467,613 S | 12/2002 | Indegno et al. | |
| 6,488,665 B1 | 12/2002 | Severin et al. | |
| 6,503,013 B2 | 1/2003 | Strauss | |
| 6,505,985 B1 | 1/2003 | Hidle et al. | |
| 6,523,550 B2 | 2/2003 | McCormick | |
| 6,533,484 B1 | 3/2003 | Osei et al. | |
| 6,536,975 B1 | 3/2003 | Tufts | |
| 6,546,588 B1 | 4/2003 | Black | |
| 6,547,468 B2 | 4/2003 | Gruenbacher et al. | |
| 6,595,940 B1 | 7/2003 | D'Alessio et al. | |
| 6,595,969 B1 | 7/2003 | Emerit et al. | |
| D481,165 S | 10/2003 | Angeletta | |
| D481,166 S | 10/2003 | Angeletta | |
| 6,672,784 B2 | 1/2004 | Baumann et al. | |
| 6,682,695 B1 | 1/2004 | MacPhee et al. | |
| 6,708,822 B1 | 3/2004 | Muni | |
| D490,561 S | 5/2004 | Angeletta | |
| D490,562 S | 5/2004 | Angeletta | |
| 6,729,786 B1 | 5/2004 | Tufts et al. | |
| 6,773,189 B1 | 8/2004 | Tsaur | |
| D498,021 S | 11/2004 | Angeletta | |
| 6,902,335 B2 | 6/2005 | Bergey et al. | |
| 6,910,822 B2 | 6/2005 | Hidle et al. | |
| 6,916,133 B2 | 7/2005 | Hoang et al. | |
| 6,929,475 B1 | 8/2005 | Dragan | |
| 6,960,041 B2 | 11/2005 | Tsaur | |
| D512,794 S | 12/2005 | Angeletta | |
| 6,991,393 B2 | 1/2006 | Tufts et al. | |
| 6,991,394 B2 | 1/2006 | Tufts et al. | |
| 6,992,233 B2 | 1/2006 | Drake et al. | |
| D519,283 S | 4/2006 | Watson | |
| 7,040,827 B2 | 5/2006 | Gueret | |
| D527,489 S | 8/2006 | Angeletta | |
| 7,090,422 B2 | 8/2006 | Baumann et al. | |
| D527,842 S | 9/2006 | Angeletta | |
| 7,108,440 B1 | 9/2006 | Gruenbacher et al. | |
| D536,481 S | 2/2007 | Angeletta | |
| 7,182,536 B2 * | 2/2007 | Tufts et al. | 401/133 |
| 7,201,525 B2 | 4/2007 | Mohiuddin | |
| D543,658 S | 5/2007 | Angeletta | |
| D547,003 S | 7/2007 | Angeletta | |
| 7,261,701 B2 | 8/2007 | Davis et al. | |
| D558,393 S | 12/2007 | Angeletta | |
| D566,330 S | 4/2008 | Angeletta | |
| 7,377,710 B2 | 5/2008 | Baumann et al. | |
| 2001/0012851 A1 | 8/2001 | Lundy et al. | |
| 2001/0050083 A1 | 12/2001 | Marchitto et al. | |
| 2001/0055511 A1 | 12/2001 | Baumann et al. | |
| 2002/0044816 A1 | 4/2002 | Strauss | |
| 2002/0076255 A1 | 6/2002 | Hoang et al. | |
| 2002/0114657 A1 | 8/2002 | Gueret | |
| 2003/0086747 A1 | 5/2003 | Baumann et al. | |
| 2003/0095826 A1 | 5/2003 | Policicchio et al. | |
| 2003/0123919 A1 | 7/2003 | Gueret | |
| 2004/0068218 A1 | 4/2004 | Davis et al. | |
| 2004/0071494 A1 | 4/2004 | Staniforth et al. | |
| 2004/0074033 A1 | 4/2004 | Steinberg | |
| 2004/0086321 A1 | 5/2004 | Burkholz et al. | |
| 2004/0114988 A1 | 6/2004 | Baumann et al. | |
| 2004/0162533 A1 | 8/2004 | Alley | |
| 2004/0223801 A1 | 11/2004 | Detwiler et al. | |
| 2004/0230168 A1 | 11/2004 | Keaty, Jr. et al. | |
| 2004/0240927 A1 * | 12/2004 | Hoang et al. | 401/133 |
| 2004/0253039 A1 | 12/2004 | Stenton | |
| 2004/0265388 A1 | 12/2004 | Zhang et al. | |
| 2005/0003178 A1 | 1/2005 | Detert et al. | |
| 2005/0047845 A1 | 3/2005 | White et al. | |
| 2005/0049538 A1 | 3/2005 | Trevillot | |
| 2006/0072962 A1 | 4/2006 | Cybulski et al. | |
| 2006/0115520 A1 | 6/2006 | Vanek et al. | |
| 2006/0147250 A1 | 7/2006 | Tereschouk | |
| 2006/0247568 A1 | 11/2006 | Stenton | |
| 2007/0014947 A1 | 1/2007 | Mengel et al. | |

(56) References Cited

U.S. PATENT DOCUMENTS

| | | |
|---|---|---|
| 2007/0020029 A1 | 1/2007 | Baumann et al. |
| 2007/0147946 A1 | 6/2007 | Cybulski et al. |
| 2007/0147947 A1* | 6/2007 | Stenton et al. ............ 401/133 |
| 2008/0119801 A1 | 5/2008 | Moore |
| 2009/0008021 A1 | 1/2009 | Detert et al. |
| 2009/0324319 A1 | 12/2009 | Cocke et al. |

FOREIGN PATENT DOCUMENTS

| | | |
|---|---|---|
| DE | 19860759 | 6/2000 |
| EP | 0 232 596 A1 | 8/1987 |
| EP | 0 507 317 A2 | 10/1992 |
| EP | 1 721 582 A1 | 11/2006 |
| GB | 2 272 644 A | 5/1994 |
| JP | S57068780 | 4/1982 |
| JP | 1080375 | 3/1989 |
| JP | 7307311 | 11/1995 |
| JP | H09500805 | 1/1997 |
| JP | 9028716 | 2/1997 |
| JP | 2004-515285 | 5/2004 |
| RU | 2 248 816 C2 | 8/2003 |
| RU | 2001134504 A | 8/2003 |
| WO | WO 95/03734 | 2/1995 |
| WO | WO 99/63934 | 12/1999 |
| WO | WO 01/74437 A1 | 10/2001 |
| WO | WO 02/46089 | 6/2002 |
| WO | WO 03/024617 A1 | 3/2003 |
| WO | WO 03/076000 | 9/2003 |
| WO | WO 03/092784 A1 | 11/2003 |
| WO | WO 2004/094494 | 11/2004 |
| WO | WO 2004/110545 A1 | 12/2004 |
| WO | WO 2005/099808 A1 | 10/2005 |
| WO | WO 2006/055397 | 5/2006 |
| WO | WO 2006/131747 A1 | 12/2006 |

OTHER PUBLICATIONS

Office Action in the corresponding Japanese Patent Application No. 2011-544596 dated Jun. 26, 2012, 8 pages.
Extended European Search Report in European Patent Application No. 13158412.0, mailed Jul. 16, 2013 (8 pages).
Office Action dated Jul. 8, 2014, from the Mexican Patent Office for Mexican Patent Application No. MX/a/2011/006968.
Notice of Allowance dated May 20, 2014, from the Russian Patent Office for corresponding Russian Patent Application No. 2011130842.

* cited by examiner

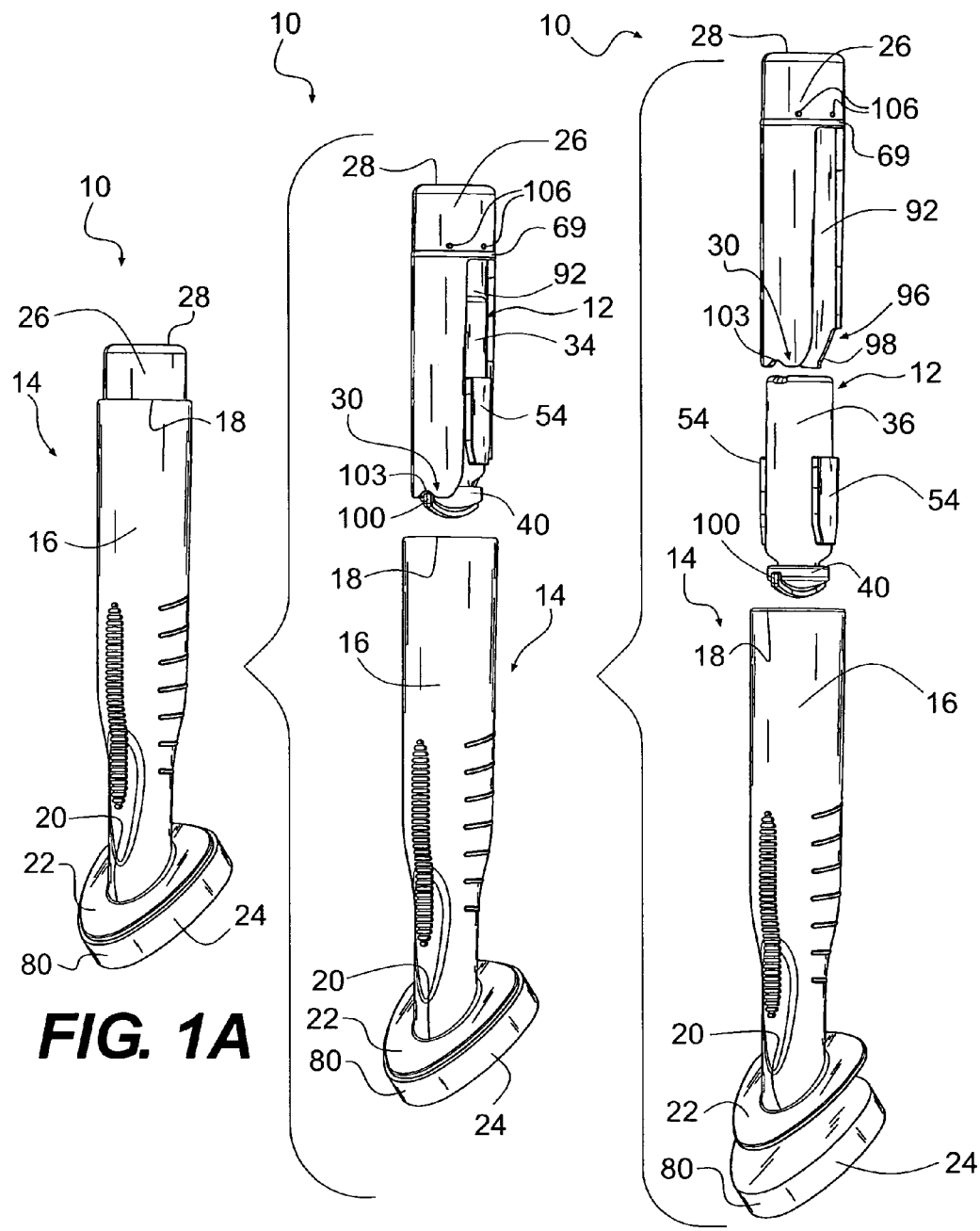

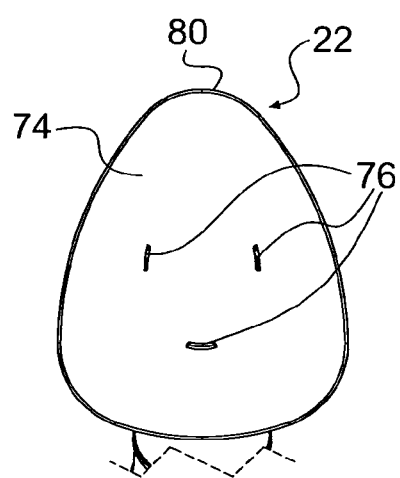
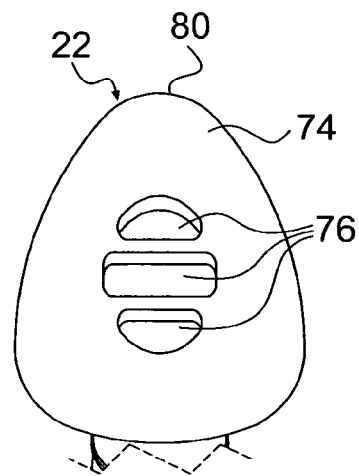
FIG. 4A  FIG. 4B
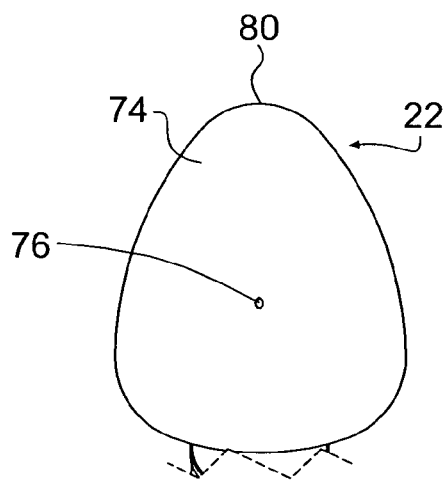
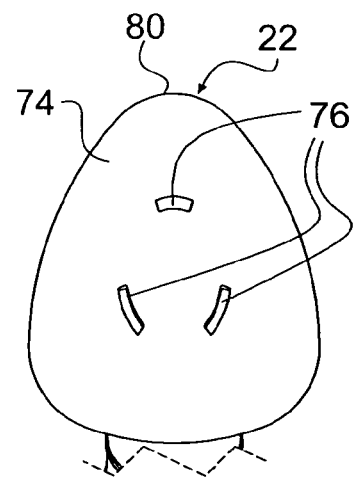
FIG. 4C  FIG. 4D

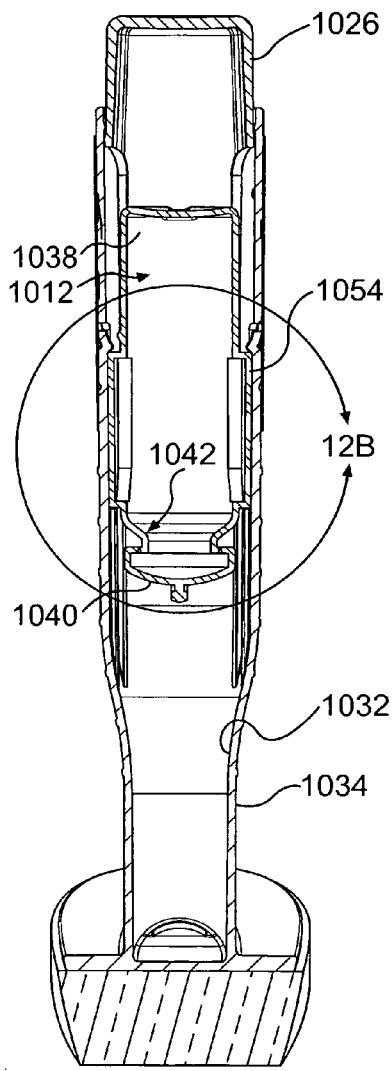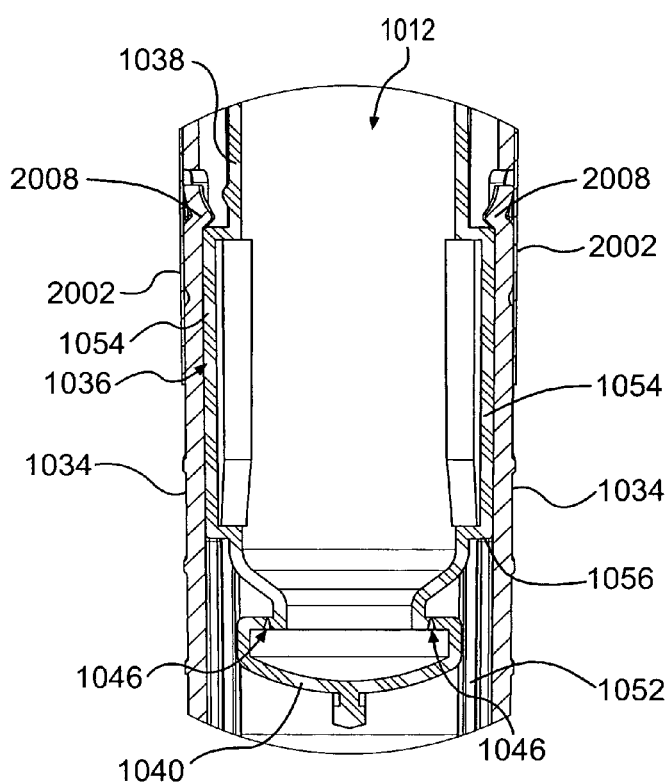
FIG. 12A
FIG. 12B

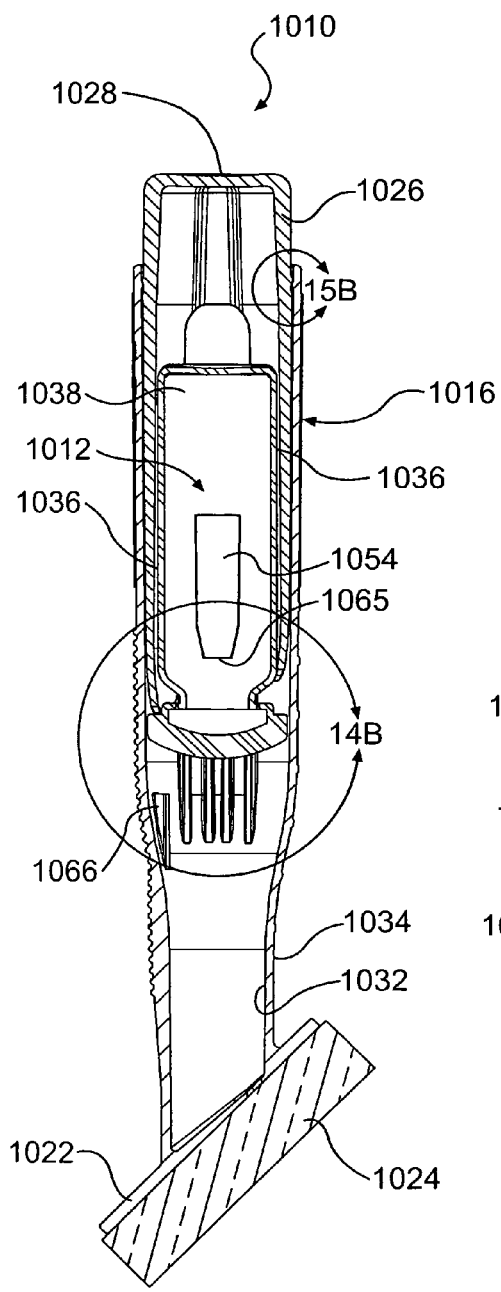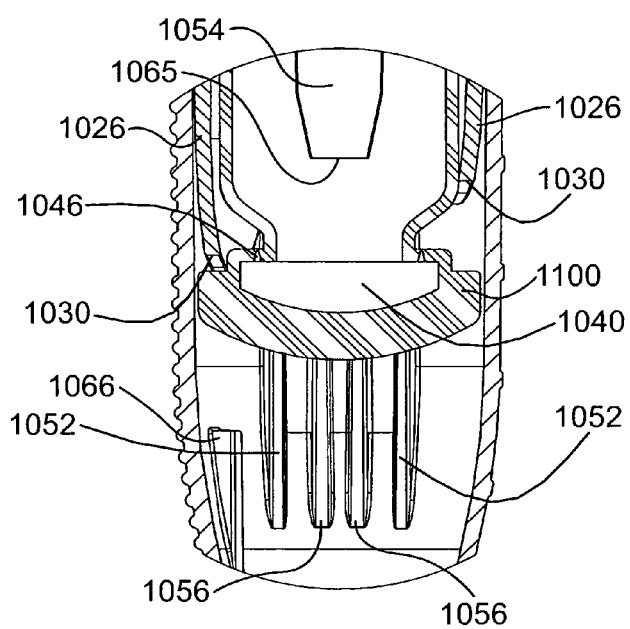
FIG. 14A
FIG. 14B

FLUID APPLICATION DEVICE AND METHOD

This application claims the benefit of U.S. Provisional Application No. 61/141,544, filed Dec. 30, 2008.

TECHNICAL FIELD

The present application relates to an apparatus and method for fluid application.

BACKGROUND

Preparation of patients for various medical procedures, e.g., surgery, typically includes application of a topical solution (or fluid), e.g., an antiseptic solution, to sanitize the area targeted for medical procedures. Topical solutions may be applied to the targeted area by saturating a sponge-like material with the solution and using a handheld device, for example a pair of forceps or a hemostat, to direct the saturated sponge to the targeted area. The sponges or foam materials are typically soaked in a fluid contained within an open pan or other container.

In certain instances, existing devices used to apply solutions exhibit various disadvantages. For example, typical applicators utilize sponges that do not retain fluid efficiently, resulting in leakage. As a result, preparation of targeted areas for antiseptic cleaning becomes a messy procedure. In addition, leakage of various fluids onto areas outside of the targeted areas can lead to pooling of the various fluids, which may cause irritation, discomfort, and/or other undesirable conditions.

Another example of a disadvantage involves the difficulty of dispensing a desired dose of fluid at the targeted area. During fluid application, in certain instances, it may be desirable to control the amount of fluid, e.g., antiseptic solution, that is dispensed from the applicator. However, because existing applicators dispense fluid inefficiently, the precise amount of solution delivered to the targeted area may be difficult to determine. This may result in either more or less solution applied to the targeted area than is desired. In addition, typical applicators utilize foams and/or fluid delivery systems that fail to timely dispense a precise amount of fluid. For example, certain applicators with internal ampoules that store fluid take time for the fluid to saturate the sponge and thus be available for application to the patient. This can result in unpredictable and imprecise dispensing of the desired solution.

SUMMARY

In certain aspects, the present disclosure is directed to an applicator device for applying a fluid. The applicator device may include a handle. The handle may comprise an elongate hollow body having a proximal end and a distal end and at least one longitudinal, interior rib disposed on an inner surface of an outer wall of the hollow body, wherein the at least one interior rib is configured to orient and guide a container for containing the fluid when the container is disposed within the hollow body. In addition, the applicator device may include a base at the distal end of the hollow body. Further, the applicator device may include an applicator pad coupled to the base.

In some aspects, the present disclosure is directed to an applicator device for applying a fluid. The applicator device may include a handle. The handle may include an elongate hollow body having a proximal end and a distal end. The applicator device may further include a base at the distal end of the hollow body, and an applicator pad coupled to the base. In addition, the applicator device may include an actuator sleeve having a proximal end, a distal end, and an outer wall having an outer surface, the actuator sleeve being configured to be inserted within the hollow body so that the outer surface of the outer wall of the actuator sleeve is disposed within the inner surface of the outer wall of the hollow body. The actuator sleeve may be configured to be actuated to release the fluid to the applicator pad from a container configured to be inserted into the hollow body. The actuator sleeve may include at least one notch extending from the distal end of the actuator sleeve toward the proximal end of the actuator sleeve. The notch may be configured to interact with a corresponding outward protrusion on the container.

In various aspects, the present disclosure is directed to a system for applying a fluid. The system may include a container configured to contain the fluid. In addition, the system may include an applicator device for applying the fluid. The applicator device may comprise an elongate hollow body having a proximal end and a distal end, the hollow body being configured to have the container inserted therein. The applicator device may further comprise a base at the distal end of the elongate hollow body and an applicator pad configured to be coupled to the base. Also, the applicator device may include an annular actuator sleeve having a proximal end and a distal end configured to be installed within the hollow body between an inner surface of an outer wall of the hollow body and an outer wall of the container so that longitudinal translation of the actuator sleeve releases the fluid from the container, allowing the fluid to flow to the applicator pad. The actuator sleeve may include one or more longitudinal projections projecting distally and configured to interact with a cap portion on a distal end of the container to remove the cap portion from the container to release the fluid from the container.

In some aspects, the present disclosure is directed to a method for applying a fluid to a surface. The method may include releasing fluid from a container disposed within a hollow body to an applicator pad coupled to a base of the hollow body at a distal end of the hollow body, by longitudinally translating, within the hollow body, an actuator sleeve having a proximal end, a distal end, and an outer wall having an outer surface. Upon the longitudinal translation, the outer surface of the outer wall of the actuator sleeve may be disposed within an inner surface of an outer wall of the hollow body, and the actuator sleeve may interact with a cap portion on a distal end of the container to remove the cap portion from the container to release the fluid from the container.

In some aspects, the present disclosure is directed to a system for applying a fluid, comprising a container configured to contain the fluid and an applicator device for applying the fluid. The applicator device may comprise an elongate hollow body having a proximal end and a distal end, the hollow body being configured to have the container inserted therein. The applicator device may also include a base at the distal end of the elongate hollow body. In addition, the applicator device may include an annular actuator sleeve having a proximal end and a distal end configured to be installed within the hollow body between an inner surface of an outer wall of the hollow body and an outer wall of the container such that longitudinal translation of the actuator sleeve within the hollow body releases the fluid from the container, allowing the fluid to flow to the applicator pad. In some embodiments, the container may include a flat side and the actuator sleeve may include a thicker, reinforced portion, which corresponds with the inset side of the container.

In some aspects, the present disclosure is directed to a system for applying a fluid, comprising a container configured to contain the fluid and an applicator device for applying the fluid. The applicator device may comprise an elongate hollow body having a proximal end and a distal end, the hollow body being configured to have the container inserted therein. The applicator device may also include a base at the distal end of the elongate hollow body and an annular actuator sleeve. The actuator sleeve may have a proximal end and a distal end configured to be installed within the hollow body between an inner surface of an outer wall of the hollow body and an outer wall of the container such that longitudinal translation of the actuator sleeve within the hollow body causes the actuator sleeve to act upon the container to release the fluid from the container, allowing the fluid to flow to the applicator pad. In addition, the container may include a main body portion, a cap portion, and a neck portion between the main body portion and the cap portion. The neck portion may comprise a frangible portion and a hinge element disposed opposite the frangible portion. The hinge element may be configured to maintain a connection between the main body portion and the cap portion after the frangible portion fractures, thus allowing the cap portion to flip open.

BRIEF DESCRIPTION OF THE DRAWINGS

FIGS. 1A-1C illustrate perspective views of an exemplary embodiment of an applicator system for applying a fluid in various stages of assembly;

FIGS. 4A-4H illustrate several exemplary disclosed embodiments of a base of an applicator device;

FIG. 12A illustrates a cross-sectional side view of an applicator system according to an exemplary disclosed embodiment;

FIG. 12B illustrates a close-up view of a portion of the applicator system shown in FIG. 12A;

FIG. 14A illustrates a cross-sectional side view of an exemplary assembled applicator system in a pre-activated state;

FIG. 14B illustrates a close-up view of a portion of the applicator system shown in FIG. 14A in the pre-activated state;

DESCRIPTION OF VARIOUS EMBODIMENTS

Figure 2A:
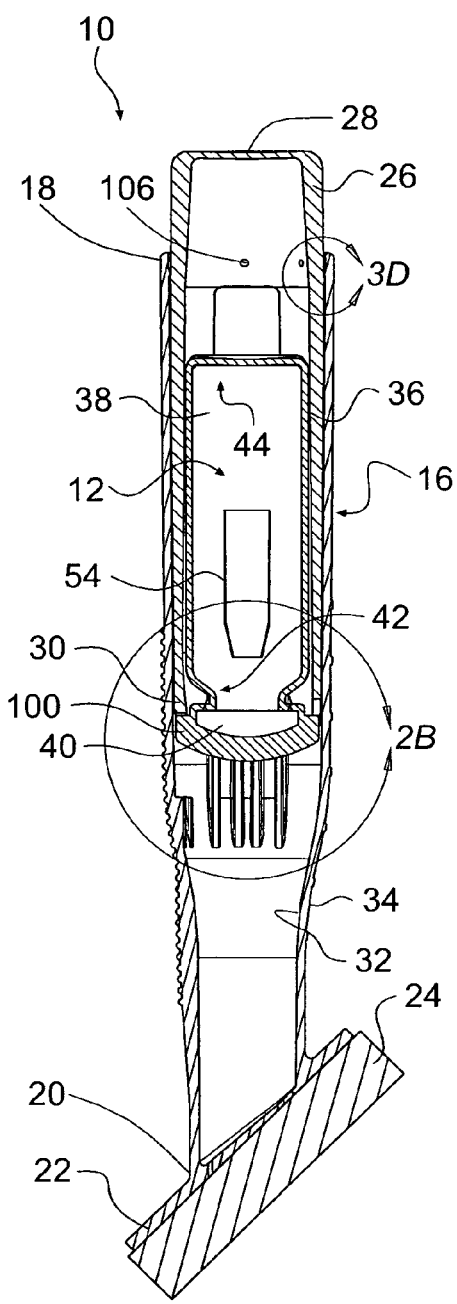
FIG. 2A illustrates a cross-sectional side view of an applicator system according to an exemplary disclosed embodiment.

In this application, the use of the singular includes the plural unless specifically stated otherwise. In this application, the use of "or" means "and/or" unless otherwise stated. Furthermore, the use of the term "including," as well as other forms, such as "includes" or "included," is not limiting. Also, terms such as "element" or "component" encompass both elements and components comprising one unit and elements and components that comprise more than one unit unless specifically stated otherwise The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The disclosed applicator may be configured to dispense/apply any liquid with a viscosity suitable to allow passage through, and dispensing by, the disclosed device. In some embodiments, the disclosed applicator may be utilized to dispense/apply an antiseptic fluid. The term "antiseptic fluid," as used herein, refers to a liquid that, in certain embodiments, may be used to sanitize a region in preparation for various medical procedures.

Reference will now be made in detail to the drawings. Wherever possible, the same reference numbers will be used throughout the drawings to refer to the same or like parts.

FIGS. 1A-1C illustrate, in various stages of assembly, a system 10 for applying a fluid. FIG. 1A shows system 10 fully assembled. As shown in FIGS. 1B and 1C, system 10 may include a container 12 configured to contain a fluid. In addition, system 10 may include an applicator device 14 configured to apply a fluid to a surface. Applicator device 14 may include a handle comprising an elongate hollow body 16. Hollow body 16 may also include a proximal end 18 and a distal end 20. Hollow body 16 may be configured to have container 12 inserted therein. (See, e.g., FIG. 2A.) Applicator device 14 may include a base 22 at distal end 20 of hollow body 16 and an applicator pad 24 coupled to base 22. In addition, applicator device 14 may include an annular actuator sleeve 26 having a proximal end 28 and a distal end 30 and may be configured to be installed within hollow body 16 between an inner surface 32 (see, e.g., FIG. 2A) of an outer wall 34 of hollow body 16 and an outer wall 36 of container 12 such that actuation of actuator sleeve 26 may release the fluid from container 12, allowing the fluid to flow to applicator pad 24.

Container

Figure 2B:
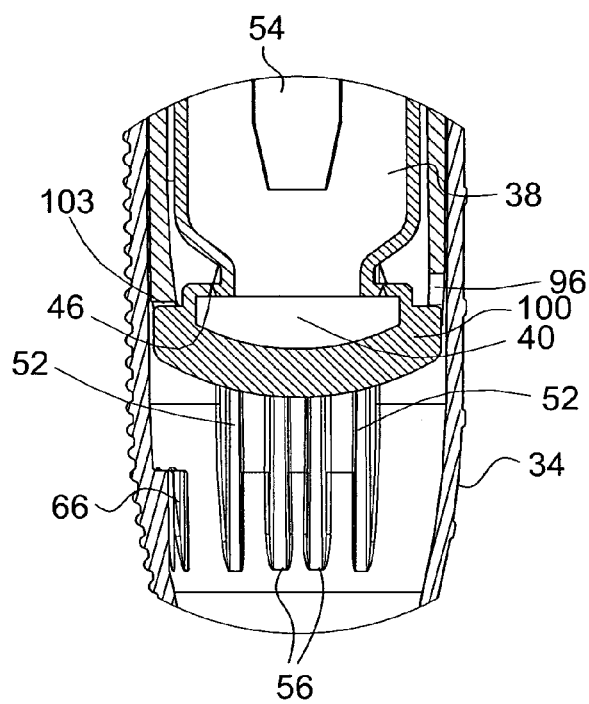
FIG. 2B illustrates a close-up view of a portion of the applicator system shown in FIG. 2A.

As shown in FIGS. 2A and 2B, container 12 may include a main body portion 38 and cap portion 40 at a distal end 42 of main body portion 38. Container 12 may be configured to be inserted into hollow body 16 with distal end 42 of container 12 oriented toward distal end 20 of hollow body 16, as shown in FIG. 2A. In some embodiments, cap portion 40 may be removable from main body portion 38. For example, cap portion 40 may be press-fit, snap-fit, threaded, etc. onto, or into, main body portion 38. In certain embodiments, cap portion 40 may be integrally formed with main body portion 38. In some embodiments, container 12 may include a frangible portion 46, as shown in FIG. 2B, between main body portion 38 and cap portion 40, wherein frangible portion 46 is configured to break upon displacement of cap portion 40 by actuator sleeve 26. That is, in some embodiments, pushing cap portion 40 off of container 12, involves breaking container 12 at frangible portion 46. Once cap portion 40 is removed from container 12, the opening created at distal end 42 of container 12 may be of a size and shape that allows container 12 to self-vent and drain. In addition, in some embodiments, container 12 may be pierced at its distal end to allow fluid to drain.

In certain embodiments, cap portion 40 may be configured to be pushed off container 12 in a longitudinal direction within hollow body 16 upon the longitudinal translation of actuator sleeve 26. In some embodiments, cap portion 40 may be configured to be twisted to remove cap portion 40 from container 12. In certain embodiments, cap portion 40 may be configured to be removed from container 12 using both a pushing and a twisting motion. In some alternative embodiments, cap portion 40 may be pulled off. In such embodiments, actuator sleeve 26 may include a ring element, not shown, configured to pull on a portion of container 12.

Container 12 may be formed of any type of material that is suitable for forming a fluid-holding container with a frangible or removable cap portion. In some embodiments, container 12 may be a blow-fill-seal container. Exemplary materials from which container 12 may be made include polyethylene, polypropylene, nylon, and blends of such materials.

In certain embodiments, the liquid contained in container 12 may be an antiseptic solution containing an active ingredient. Various antiseptic solution active ingredients are known in the art, including, but not limited to, ethanol, isopropyl alcohol, other alcohols, and combinations thereof; benzalkonium chloride; benzethonium chloride; chlorhexidine gluconate; chlorhexidine gluconate with alcohol; chloroxylenol; cloflucarban; fluorosalan; hexachlorophene; hexylresorcinols; iodine-containing compounds; povidone iodine; povidone iodine with alcohol, and combinations thereof.

In certain embodiments, the antiseptic solution may include a biguanide derivative and/or salts thereof, e.g., olanexidine [1-(3,4-dichlorobenzyl)-5-octylbiguanide] and salts thereof, as the active ingredient, as disclosed, for example in U.S. Pat. No. 5,376,686. The antiseptic solution may also incorporate certain surfactants, for example, polyoxyethylene-based nonionic surfactants, and/or alcohols, for example, ethanol, isopropyl alcohol, and other alcohols, and/or water, in varying amounts. Useful surfactants are known to one skilled in the art, for example, Poloxamer 124 (a/k/a Polyoxypropylene-polyoxyethylene Block Copolymer 124), which is available as Polyoxyethylene(20) polyoxypropylene(20) glycol from Asahi Denka Co., Ltd., Japan, POE (9) lauryl ether (available as 'BL-9EX' from Nikko Chemicals Co., Ltd., Tokyo, Japan), POE (10) lauryl ether, also known as nonoxynol-10, or NP-10, (available as 'Emulin NL-100' from Sanyo Chemical Industries, Ltd., Kyoto Japan).

In certain embodiments, the antiseptic solution may include an active ingredient and a polyoxyethylene-based nonionic surfactant in various concentrations. In some embodiments, the polyoxyethylene-based nonionic surfactant may be present at a concentration of about 0.05 to about 16% (w/v).

In certain embodiments, the topical antiseptic may include a biguanide derivative and/or salts thereof, which may be present at a concentration of about 0.05 to about 5.0% (w/v of biguanide base). In some embodiments, the biguanide derivative or salt thereof may be olanexidine [1-(3,4-dichlorobenzyl)-5-octylbiguanide] or a salt thereof. In some embodiments, the salt may be a gluconate.

In some embodiments of system 10 applicator device 14 may be provided in ready to use form. For example, applicator device 14 may be stored, packaged, and/or shipped, etc. with applicator pad 24 attached to base 22 and with container 12 and actuator sleeve 26 inserted within hollow body 16, as shown in FIG. 2A. In such embodiments, container 12 may be pre-filled with a fluid, such as an antiseptic fluid, for example.

Hollow Body

Figure 3A:
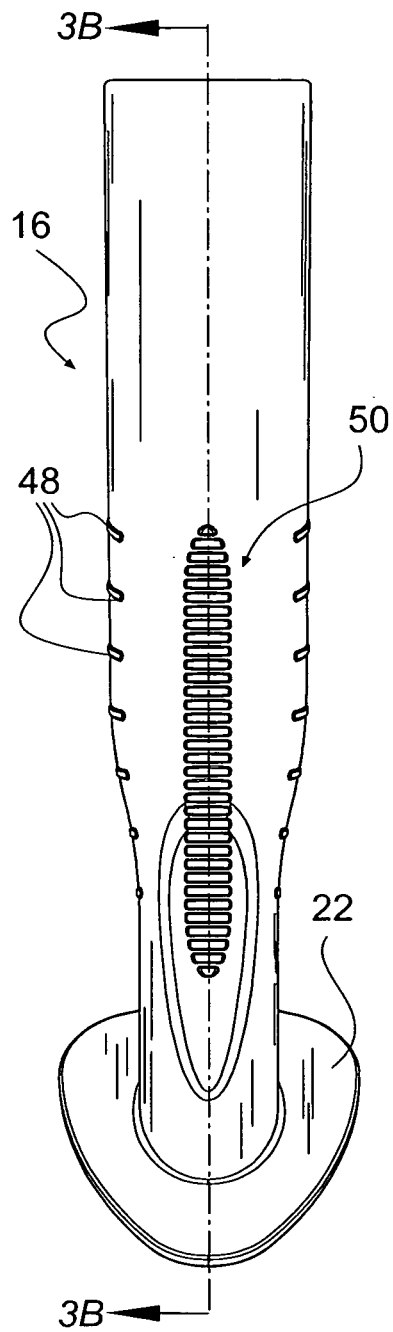
FIG. 3A illustrates a front view of a handle and base of a fluid applicator device, according an exemplary disclosed embodiment.

As illustrated by FIG. 3A, hollow body 16 may include various shaping, sizing, and/or one or more exterior gripping features to facilitate manipulation of applicator device 10 by a user. For example, hollow body 16 may include indentations, protrusions, texture, rubberized material, etc., to promote secure gripping of hollow body 16. For example, as shown in FIG. 3A, hollow body 16 may include one or more protruding gripping members 48 and/or a textured gripping strip 50. In some embodiments more than one textured gripping strip 50 may be provided. Also, in some embodiments, hollow body 16 may include an ergonomic bend (not shown) and/or a widened exterior portion configured to conform with contours of a hand palm.

Hollow body 16 and/or base 22 may be made of any suitable material including, but not limited to, metals, metal-alloys, plastics and other polymers, including, for example, polycarbonate, nylon, modified acrylics, Methylmethacrylate-Acrylonitrile-Butadiene-Styrene (MABS), thermoplastic alloys, various composite materials, or combinations thereof. Hollow body 16 may be made by various manufacturing processes known in the art including, but not limited to, molding, injection molding, machining, casting, extruding, and/or combinations thereof.

In some embodiments, one or more components of applicator 12 may be formed of a transparent or translucent material. For example, one or more portions of hollow body 16 and/or actuator sleeve 26 may be formed of a transparent or translucent material. Transparency and/or translucency of certain components may enable observation of the quantity of fluid remaining in container 12 and/or facilitate monitoring the flow of the fluid through applicator device 14 while being dispensed.

Figure 3B:
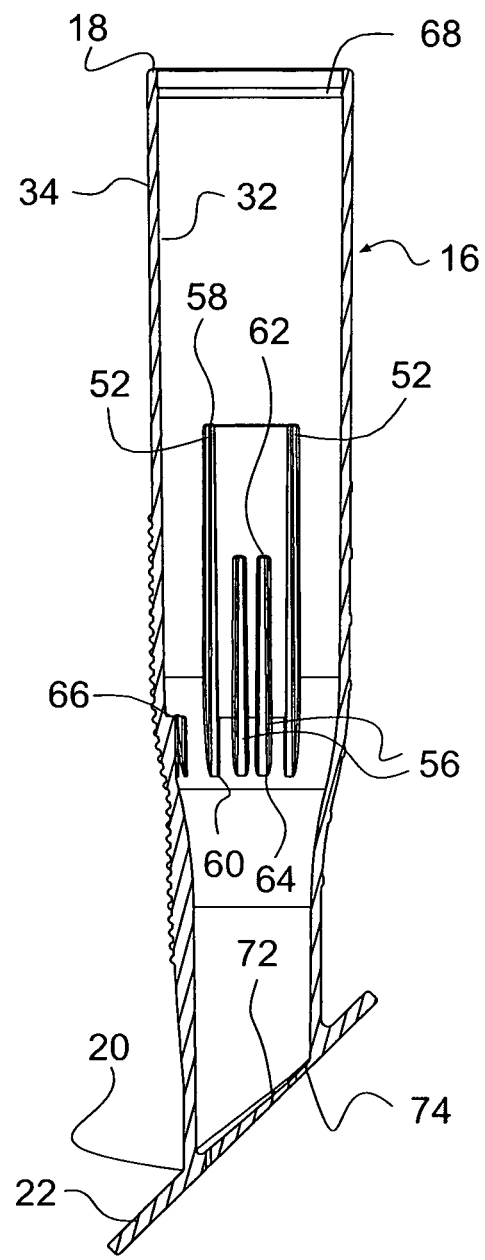
FIG. 3B illustrates a cross-sectional side view of the handle and base shown in FIG. 3A.
Figure 3C:
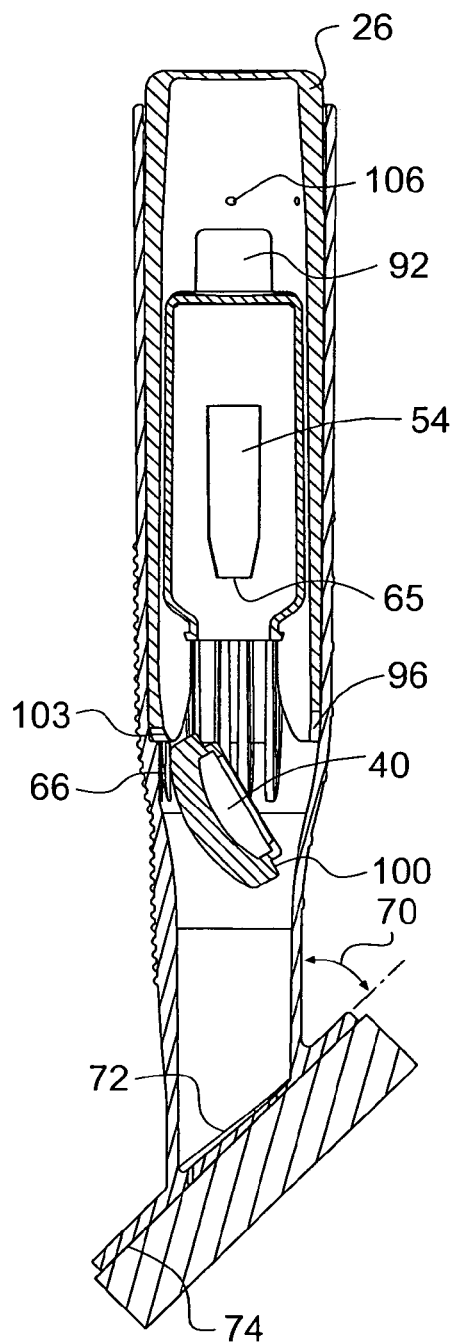
FIG. 3C illustrates a cross-sectional side view of an assembled applicator system including the handle and base shown in FIG. 3B wherein the actuator sleeve has been actuated.

Hollow body 16 may include one or more interior guiding elements configured to orient and guide container 12 when container 12 is disposed within hollow body 16. For example, as shown in FIG. 3B, hollow body 16 may include one or more longitudinal, interior guiding ribs 52 disposed on inner surface 32 of hollow body 16. Interior guiding ribs 52 may be configured to restrict rotation of container 12 within hollow body 16. For example, in some embodiments, hollow body 16 may include two substantially parallel guiding ribs 52 spaced apart from one another. In such embodiments, container 12 may include a corresponding outward protrusion 54, as shown in FIG. 3C, having a size and shape to fit within, and be guided by, guiding ribs 52. Alternatively, or additionally, hollow body 16 may include one or more grooves (not shown) for orienting and guiding container 12. For example, in certain embodiments, ribs 52 may, instead, be grooves in inner surface 32 of hollow body 16.

As also shown in FIG. 3B, hollow body 16 may include one or more longitudinal stopping ribs 56, substantially parallel to, and disposed between, guiding ribs 52. Each of guiding ribs 52 may include a proximal end 58 and a distal end 60 and each of stopping ribs 56 may have a proximal end 62 and a distal end 64. In some embodiments, proximal end 62 of each of stopping ribs 56 may be located distal to the proximal ends 58 of guiding ribs 52 and may be configured to interact with a distal end 65 (see FIG. 3C) of outward protrusion 54 on container 12 in order to stop longitudinal translation of container 12 in a distal direction within hollow body 16. Applicator device 14 may be configured so that, when longitudinal translation of container 12 in a distal direction is prevented by stopping ribs 56 and rotational translation is prevented by guiding ribs 52, longitudinal translation of actuator sleeve 26 pushes and/or twists container cap portion 40 to remove cap portion 40 from container 12, as shown in FIG. 3C.

Hollow body 16 may also include an one or more inwardly projecting protrusion 66. As shown in FIG. 3C, inwardly projecting protrusion 66 may be further configured to reorient cap portion 40 of container 12 after being broken off of container 12 by actuation of actuator sleeve 26, for example, by tilting cap portion 40 to prevent cap portion 40 from becoming lodged within hollow body 16, which could result in a blockage or reduction in flow of the fluid down to applicator pad 24. As also shown in FIG. 3C, inwardly projecting protrusion 66 may be configured to stop longitudinal translation of actuator sleeve 26. That is, inwardly projecting protrusion 66 may serve as a stop to define the limit of longitudinal translation of actuator sleeve 26.

Figure 3D:
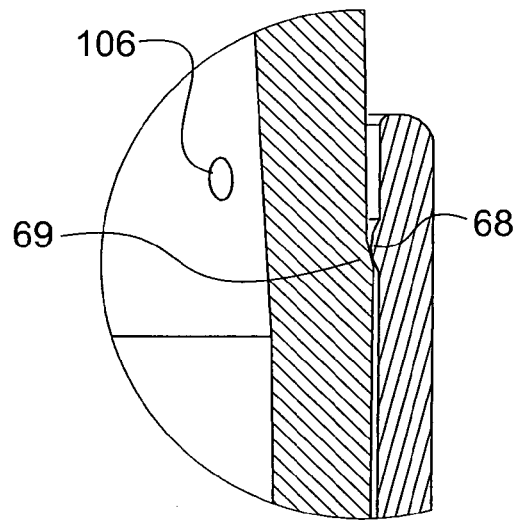
FIG. 3D illustrates a close-up view of a portion of FIG. 2A showing a sealing feature of the applicator device, according to an exemplary disclosed embodiment.

Hollow body 16 may also include one or more interior restraining and/or sealing features at proximal end 18 of hollow body 16. For example, as shown in FIGS. 3B and 3D, in some embodiments, hollow body 16 may include a circumferential restraining rib 68 configured to secure actuator sleeve 26 within hollow body 16. Restraining rib 68 may be configured to interact with corresponding features on actuator sleeve 26. For example, as shown in FIGS. 3B and 3D, actuator sleeve 26 may include a circumferential sealing rib 69 configured to not only seal the interface between actuator sleeve 26 and hollow body 16 to prevent leakage, but also interact with restraining rib 68, whereby restraining rib 68 serves as a stop preventing actuator sleeve 26 from being moved proximally beyond a point at which sealing rib 69 contacts restraining rib 68. See FIG. 3D.

Restraining rib 68 and sealing rib 69 may have the same or different profile. Although the accompanying figures show a restraining rib 68 on hollow body 16 and a sealing rib on actuator sleeve 26, in certain embodiments, the restraining rib and sealing rib could be reversed so that the sealing rib could be located on hollow body 16 and the restraining rib could be located on actuator sleeve 26. In addition, while the figures illustrate restraining and sealing features that include ribs, in some embodiments, the restraining and sealing features may include bosses, debosses, detents, etc. (Not shown.)

Base

According to certain embodiments, hollow body 16 and base 22 may define an angle 70, as shown, for example, in FIG. 3C. Although the accompanying figures illustrate embodiments wherein angle 70 is approximately 45 degrees, hollow body 16 and base 22 may define any angle within the range of 0 to 180 degrees.

As shown in FIG. 3B, base 22 may include an inner surface 72 and an outer surface 74 to which applicator pad 24 is configured to be affixed. As shown in FIGS. 4A through 4H, base 22 may include one or more perforations 76. Applicator pad 24 may be configured to be attached to base 22 over perforations 76. Perforations 76 may allow flow of the fluid from hollow body 16 to applicator pad 24.

Figure 4E:
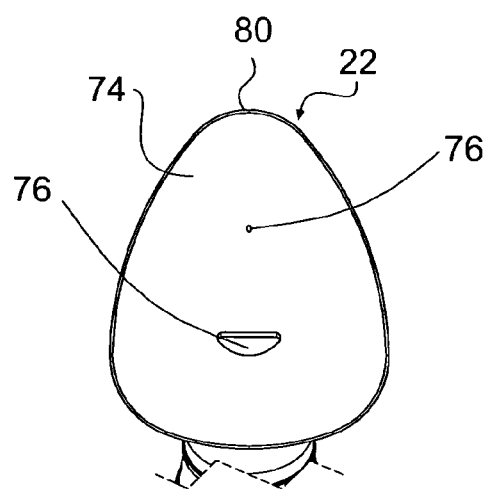
Figure 4F:
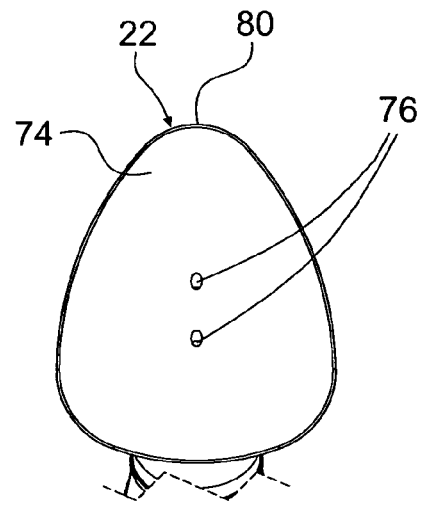
Figure 4G:
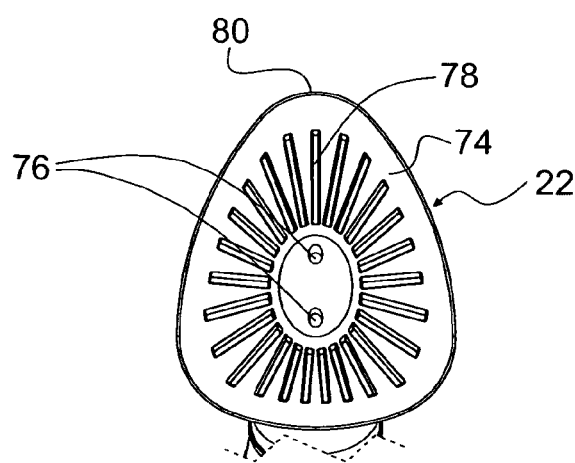
Figure 4H:
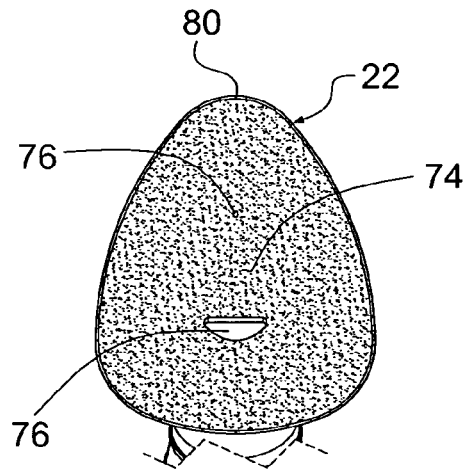

In some embodiments, outer surface 74 may include one or more channels 78, as shown in FIG. 4G. Channels 78 may be configured to distribute the fluid to different portions of applicator pad 24. Also, in some embodiments, outer surface 74 of base 22 may be textured, as shown in FIG. 4H. Texture may not only promote attachment of applicator pad 24 to base 22, but also may facilitate distribution of fluid to different parts of applicator pad 24. In addition, texture and/or other surface treatments may be added to outer surface 74 of base 22 in order to reduce surface energy and/or promote fluid distribution. For example, other possible surface treatments may include a hydrophilic coating, or plasma or flame treatment, as well as other surface treatments known in the art.

According to certain embodiments, base 22 may couple to hollow body 16. Base 22 may couple to hollow body 16 in a variety of ways known in the mechanical arts, including, but not limited to, attachments by hinges, adhesives, mechanical interlocks, threaded portions, press-fits, friction-fits, interference fits, slide-fits, and/or combinations thereof. According to other embodiments, base 22 may be integrally formed with hollow body 16. An integral base/handle combination may be manufactured by various processes known in the art, including, but not limited to, molding, injection molding, casting, machining, or combinations thereof.

In certain embodiments, applicator device 10 may include an interchangeable attachment between hollow body 16 and base 22. An interchangeable attachment may, for example, facilitate the use of variously sized bases on the same hollow body 16, and vice versa. This may facilitate, e.g., the use of differently-sized applicator pads with the same hollow body 16.

Base 22 may be formed in a variety of shapes and sizes. In some embodiments, the shape and/or size of base 22 may generally correspond to that of applicator pad 24. In other embodiments, base 22 and applicator pad 24 may have different shapes and/or sizes. In certain embodiments, base 22 and/or applicator pad 24 may be substantially triangular with rounded edges, as shown in the accompanying figures. This substantially triangular shape may approximate a teardrop shape, as shown. Other exemplary shapes for base 22 may include, without limitation, rectangular, circular, oval, various polygonal shapes, and/or complex shapes comprising combinations thereof. As shown in the accompanying figures, in some embodiments, the sides of the polygonal shapes may be curved, including embodiments wherein base 22 has a substantially triangular shape.

Applicator Pad

Applicator pad 24 may couple to base 22 using any of a variety of attachment mechanisms. For instance, applicator pad 24 may be attached to base 22 using any suitable method, including, for example, adhesive bonding using, for example, medical grade cyanoacrylate, UV cure adhesive, PSA films, and the like. In some embodiments, applicator pad 24 may be attached to base 22 using RF welding, heat staking, ultrasonic welding, laser welding, mechanical interlocks, hook-and-loop mechanisms (e.g., Velcro®), threaded pieces, etc., as well as combinations of these mechanisms. Accordingly, base 22 and applicator pad 24 may each be configured for attachment to one another using any of these mechanisms and, therefore, may include the appropriate features (e.g., texture, adhesive, mechanical latching/clamping elements, etc.) to enable such attachment.

As noted above, like base 22, applicator pad 24 may have any suitable shape and/or size. For example, in some embodiments, applicator pad 22 may have a substantially triangular shape with rounded edges (e.g., a teardrop type shape), as shown in the accompanying figures. This substantially triangular shape may enable applicator device 14 to be used on surfaces having a variety of contours. For example, the smaller tips at the rounded corners of the triangle, particularly the distal-most tip 80, may enable access to crevices and smaller features of a surface, while the broad, proximal end of applicator pad 24 may provide a large pad surface to enable application of fluid to larger, more gently contoured surfaces.

In some embodiments, applicator pad 24 may include a substantially hydrophobic foam. In other embodiments, Applicator pad 24 may include substantially hydrophilic foam. The disclosed applicator device may include a substantially hydrophobic or substantially hydrophilic foam. The term "substantially hydrophobic foam," as used herein refers to a polymer-based foam that does not absorb a substantial amount of water. In contrast, a definition of a substantially hydrophilic foam is provided below. For purposes of this disclosure, a substantially hydrophobic foam shall refer to any foam that is not substantially hydrophilic, as defined below.

The term "substantially hydrophilic foam," as used herein, refers to a polymer-based foam that has an affinity for water. For example, certain embodiments of the invention can utilize a polyurethane foam with an open-cell pore structure. In certain instances, the substantially hydrophilic foam can be designed for a high rate of fluid absorption such as, for example, absorption of around 20 times the weight of the foam. While not wishing to be bound by theory, a substantially hydrophilic foam can demonstrate an affinity for water through one or more mechanisms including, but not limited to, the presence of polar groups in the polymer chains that can form hydrogen bonds with water or liquids containing active protons and/or hydroxyl groups, a fine open-cell pore structure that channels liquid into the body of the foam structure by capillary forces, and/or the addition of absorbing materials, such as super absorbers and/or surfactants, to the foam matrix. Substantially hydrophilic foams that can be utilized in certain embodiments of the invention are available from organizations including the following: Foamex Innovations (Media, Pa., a.k.a. FXI), Crest Foam Industries, Inc. (Moonachie, N.J.), Rynel, Inc. (Boothbay, Me.), Avitar, Inc. (Canton, Mass., USA), Lendell Manufacturing, Inc. (Charles, Mich., USA), Copura (Denmark), and Foamtec International Co., Ltd. Thailand (Thailand). In addition, certain patents, including U.S. Pat. No. 5,135,472 to Hermann, et al., disclose substantially hydrophilic foams that may be utilized in certain embodiments of the invention.

Applicator pad 24 may include felting or may be non-felted. In addition, applicator pad 24 may include reticulation or may be non-reticulated. In some embodiments, applicator pad 24 may include multiple pad materials. In such embodiments, combinations of any of the above characteristics may be employed. For instance, in one exemplary, multi-material pad, one pad material may be hydrophobic and a second pad material may be hydrophilic.

Figure 5A:
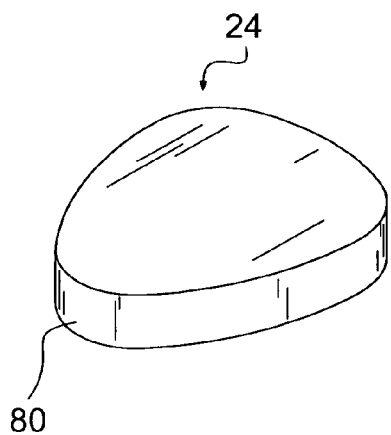
FIGS. 5A-5D illustrate several exemplary disclosed embodiments of applicator pads.
Figure 5B:
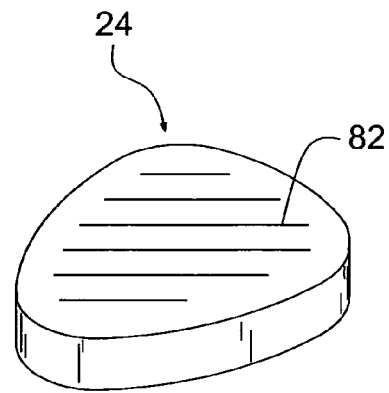

Applicator pad 24 may be formed of a single material or of multiple materials, may include a single layer or multiple layers, and/or may or may not include slits to facilitate distribution and flow of fluid through applicator pad. FIGS. 5A-5D illustrate several exemplary embodiments of applicator pad 24 having various combinations of the above-listed features. For example, in some embodiments, applicator pad 24 may comprise a single layer and no slits, as shown in FIG. 5A. In other embodiments, applicator pad 24 may comprise a single layer, which may include slits 82, as shown in FIG. 5B. As illustrated in FIG. 5B, applicator pad 24 may include multiple slits. Further, slits 82 may be provided in a pattern. For example, FIG. 5B shows a pattern of substantially parallel slits 82 oriented at an angle.

Figure 5C:
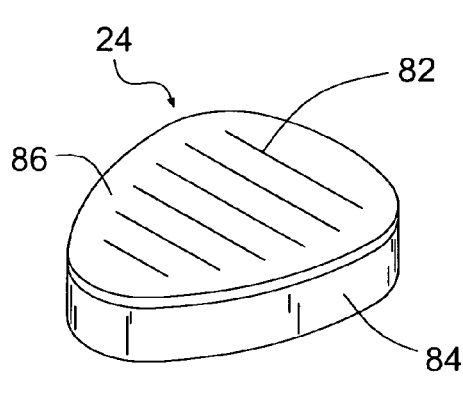
Figure 5D:
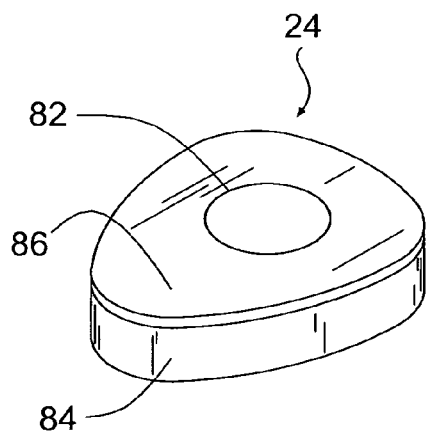

In certain embodiments, applicator pad 24 may include multiple layers. As shown in FIGS. 5C and 5D, applicator pad 24 may comprise a base layer 84 and a laminate layer 86. Slits 82 may be provided in base layer 84 and/or in laminate layer 86. FIGS. 5C and 5D illustrate embodiments wherein slits 82 are provided in at least laminate layer 86. FIG. 5C shows a pattern of substantially parallel slits 82 similar to those in FIG. 5B. FIG. 5C illustrates a pattern wherein slits 82 are oriented in a generally lateral direction, as opposed to those in FIG. 5B, which are oriented at an angle. Slits 82 may be disposed at any angle. Slits 82 may be provided in any of a number of shapes, such as slit 82 in FIG. 5D, which is generally circular. Slits 82 may also be formed in other various shapes including, but not limited to, circles, ovals, polygons, etc. Slits 82 may be formed in any suitable process, for example, by die/kiss cutting.

In some embodiments, each layer may be formed of a different pad material. In certain embodiments, applicator pad 24 may include at least one abrasion layer. In certain applications, an abrasion layer may be used to abrade an area targeted for treatment, for example the epidermis. Abrasion may be performed before, during, and/or after dispensing the fluid. In certain embodiments, abrasion may cause a loosening of certain biologic materials, for example body oils, body soils, and/or bacteria, to facilitate treatment of the targeted area. For example, before application of an antiseptic solution, a user may abrade the epidermis of a patient to loosen bacteria in order to improve the efficacy of the antiseptic application process. In certain embodiments, an abrasion layer may comprise more than one layer of material, which may facilitate a greater amount of abrasion and/or abrasion of harder to clean areas.

In certain embodiments, an abrasion layer may comprise various textures and/or weaves, for example, a gauze-like or foam material. In certain embodiments, an exemplary gauze-like material may be made from various materials that facilitate abrasion, including, but not limited to, cotton, rayon, nylon, and/or combinations thereof. Abrasion layer material may be chosen from a number of materials that exhibit varying degrees of abrasiveness. For foam materials, the level of abrasiveness may differ depending on, among other things, the size of the cells/pores. The skin of a premature baby can be thin and fragile, thus an applicator device that comprises an abrasion layer made from nylon or rayon may be preferable to an abrasion layer made from cotton. In certain embodiments, an abrasion layer may comprise a plurality of layers of different materials. In some embodiments, for example foam abrasion layers, the abrasion layer may be flame laminated to base 22 and/or applicator pad 24.

As illustrated in FIGS. 5C and 5D, laminate layer 86 (which may comprise an abrasion layer) may have a shape that generally corresponds to the shape of base layer 84 of applicator pad 24. However, in certain embodiments, laminate layer 86 may have various other shapes including, but not limited to, circular, oval, rectangular, triangular, polygonal, and the like, or complex shapes including one or more of the same. Layers of applicator pad 24 may be attached to one another by various attachment mechanisms including, but not limited to, adhesive bonding (e.g., using pressure sensitive adhesives), fusion bonding, flame lamination, heat staking, ultrasonic welding, etc. Certain methods for laminating and/or attaching various materials to applicator pad materials, such as foams, are known in the art. For example, U.S. patent application Ser. No. 10/829,919, U.S. Provisional Application No. 60/464,306, and PCT Serial No. US04/012474 all disclose methods and apparatuses for attaching materials to polyurethane foam.

Actuator Sleeve

Actuator sleeve 26 may be configured to be actuated to release the fluid to applicator pad 24 from container 12. FIGS. 6A-6D illustrate various exemplary embodiments of actuator sleeve 26. Actuator sleeve 26 may have an outer wall 88 having an outer surface 90. Actuator sleeve 26 may be configured to be inserted within hollow body 16 so that outer surface 90 of outer wall 88 of actuator sleeve 26 is disposed within inner surface 32 of outer wall 34 of hollow body 16. Actuator sleeve 26 may be configured to be actuated to release the fluid to applicator pad 24 from container 12. Actuator sleeve 26 may be configured to be longitudinally translated within hollow body 16 in order to release the fluid from container 12. Actuator sleeve 26 may be longitudinally translated within hollow body 16 by applying force to proximal end 28 of actuator sleeve 26. In some embodiments, proximal end 28 of actuator sleeve 26 may be contoured to provide substantially even force distribution across proximal end 28. For example, in certain embodiments, proximal end 28 of actuator sleeve 26 may have a rounded, convex surface, as shown in FIG. 6D. Such a convex surface may distribute force across proximal end 28, thereby reducing the pressure felt by a user. For example, a rounded convex surface may distribute the force across the palm of a user. In other embodiments, proximal end 28 of actuator sleeve 26 may have a concave surface (see corresponding actuator sleeve 1026 in FIG. 16D) to evenly distribute the force across, for example, the thumb or finger of a user.

In some embodiments, actuator sleeve 26 may include one or more notches 92 extending from distal end 30 of actuator sleeve 26 toward proximal end 28 of actuator sleeve 26. In such embodiments, container 12 may include a restraining feature, such as outward protrusion 54, to orient and position container 12 within hollow body 16. Such a restraining feature may be configured to fit within notch 92 in actuator sleeve 26.

In some embodiments, actuator sleeve 26 may include one or more longitudinal projections 94 projecting distally and configured to interact with cap portion 40 of container 12 to remove cap portion 40 from container 12 to release the fluid from container 12. For example, as shown in FIG. 6D, actuator sleeve 26 may include two longitudinal projections 94, which may define two notches 92. An actuator sleeve having two notches 92 may be compatible with a container 12 having two outward protrusions 54. (See FIG. 7.)

Figure 6A:
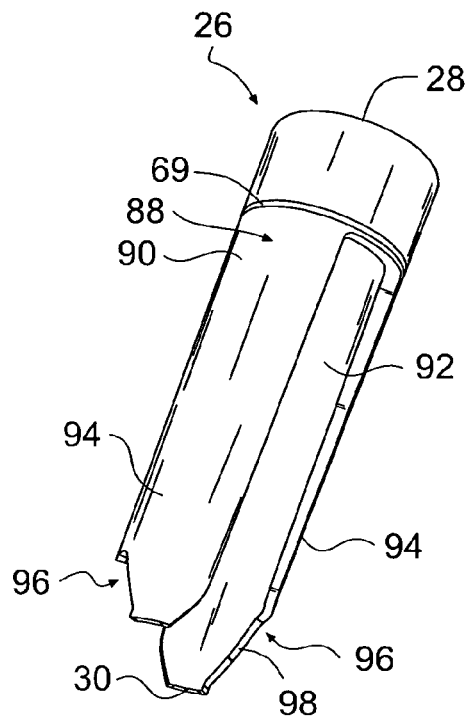
FIGS. 6A-6D illustrate several exemplary disclosed embodiments of actuator sleeves.
Figure 6B:
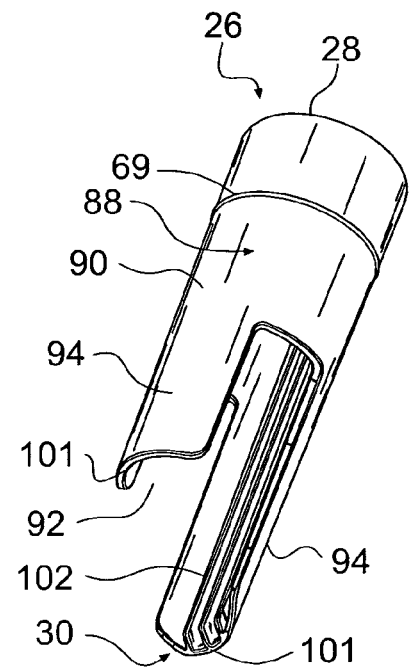
Figure 6C:
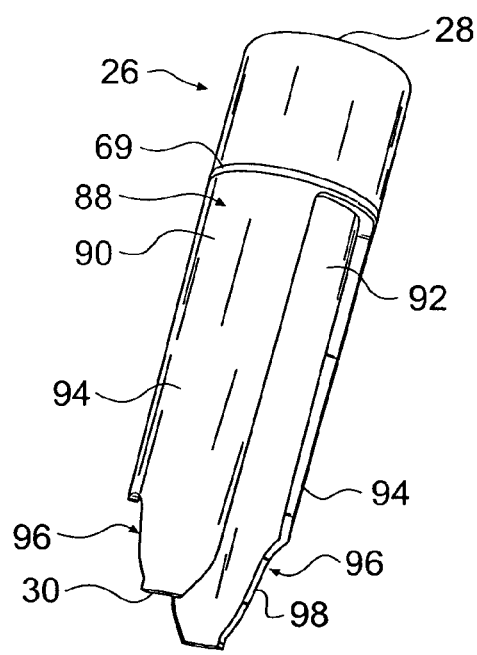
Figure 6D:
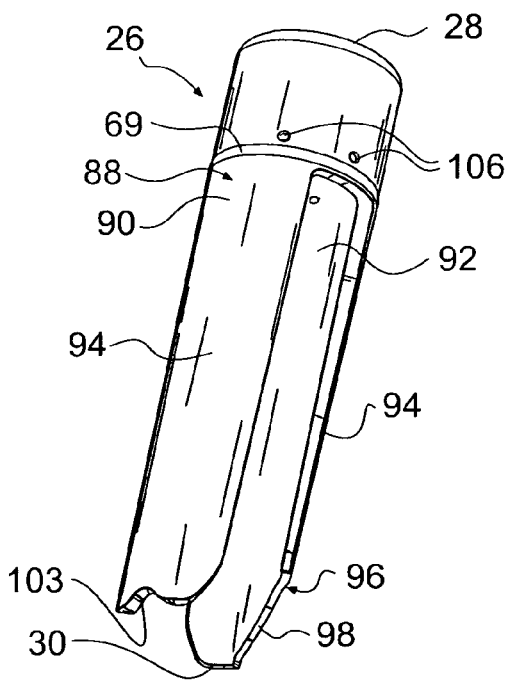
Figure 7:
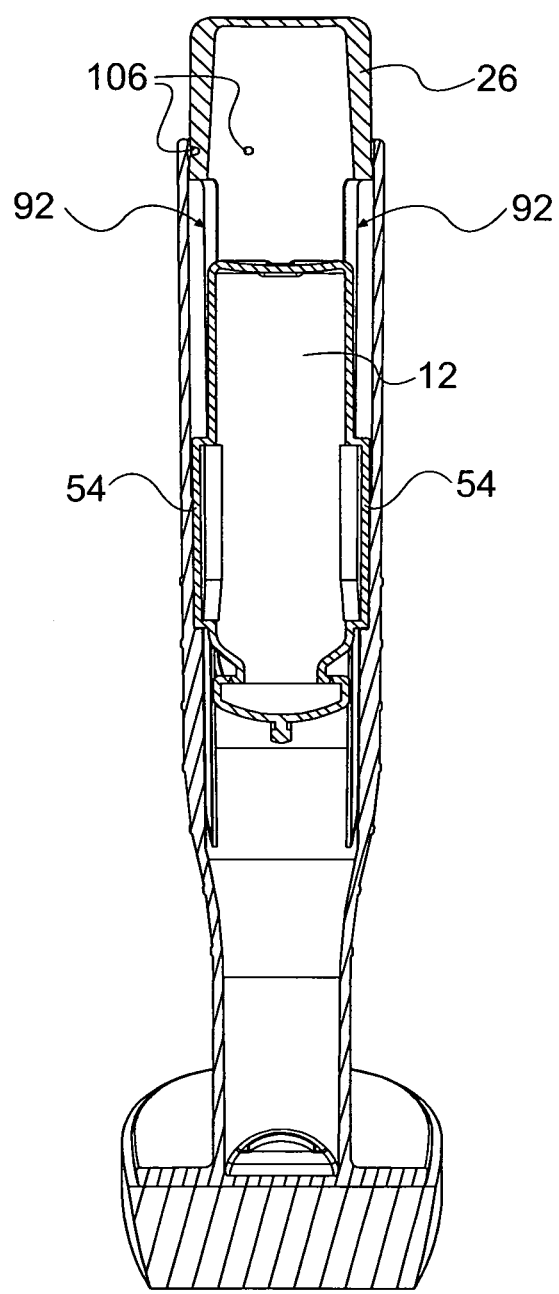
FIG. 7 illustrates a cross-sectional front view of a system for applying a fluid, according to an exemplary disclosed embodiment.

As shown in FIGS. 6A, 6C, and 6D, in some embodiments, one or more of longitudinal projections 94 may include an angled surface 96 (some embodiments may include multi-angle surfaces 98) configured to rotate cap portion 40 of container 12 upon longitudinal translation of actuator sleeve 26. In such embodiments, actuation of actuator sleeve 26 by longitudinal translation may cause cap portion 40 to rotate as a result of interaction between angled surfaces 96 and cap portion 40. For example, cap portion 40 may include protruding elements 100 (see FIG. 1C), which may interact with angled surfaces 96 of actuator sleeve 26 to rotate cap portion 40 to remove cap portion 40 from container 12, thereby releasing the fluid from container 12.

In some embodiments, longitudinal projections 94 may include substantially non-angled distal ends 101, as shown in FIG. 6B. Non-angled distal ends 101 may be configured to push protruding elements 100 distally when actuator sleeve 26 is longitudinally translated in the distal direction. As also shown in FIG. 6B, in some embodiments, longitudinal projections 94 may include inwardly projecting, longitudinal ribs 102, which terminate at distal end 30 of longitudinal projections 94. In such embodiments, ribs 102 may interact with protruding elements 100 or a similar feature of cap portion 40 to push cap portion 40 off container 12.

As shown in FIG. 6D, in some embodiments, one or more longitudinal projections 94 may include a tooth 103 configured to interact with cap portion 40 (e.g., with protruding element 100; see FIG. 1B) to prevent counter-rotation of cap portion 40 on at least one side of container 12 during longitudinal translation of actuator sleeve 26, while allowing rotation of cap portion 40 at another side of container 12 by angled surface 96 of actuator sleeve 26, in order to release the fluid from container 12. The effect of preventing counter-rotation on one side of cap portion 40 and creating rotation on another side of cap portion 40 is to rotate cap portion 40 with a center of rotation at the junction between tooth 103 and protruding element 100, rather than with a center of rotation in the center of cap portion 40. In addition, tooth 103 may function to push cap portion 40 off container 12 longitudinally. Therefore, in such an embodiment, cap portion 40 may be removed from container 12 using both a pushing and twisting motion.

In addition, actuator sleeve 26 may include a venting feature configured to permit air to enter hollow body 16 to replace the fluid as the fluid flows out of hollow body 16 into applicator pad 24, thereby maintaining atmospheric pressure within applicator device 14. For example, in some embodiments, actuator sleeve 26 may include holes 106 (or channels) at a location conducive to allowing air to easily enter applicator device 14, while limiting the possibility that fluid can leak out by means of a tortuous pathway and/or small orifice sizes. In some embodiments, holes 106 may be located at proximal end 28 of actuator sleeve 26, as shown in FIG. 6D.

Components of applicator system 10, including applicator device 14 and/or container 12, may be configured to be sterilized in various ways known in the art including, but not limited to, exposure to ethylene oxide ("$(Et)_2O$"), gamma radiation, electron beam, and/or steam. In addition, system 10 may be configured for use with aseptic fluids. In some embodiments, the fluid may be sterilized prior to filling container 1012. In other embodiments, the fluid may be sterilized while contained within container 1012. In certain embodiments, the fluid and container 1012 may be sterilized while assembled with hollow body 1016 or with applicator device 1014 as a whole. According to various embodiments, the fluid may be sterilized in various ways known in the art, including, but not limited to, filtration, exposure to gamma radiation, electron beam, and/or steam. For example, U.S. Pat. No. 6,682,695 discloses a method for sterilizing a fluid that may be consistent with certain embodiments of the invention.

Figure 8A:
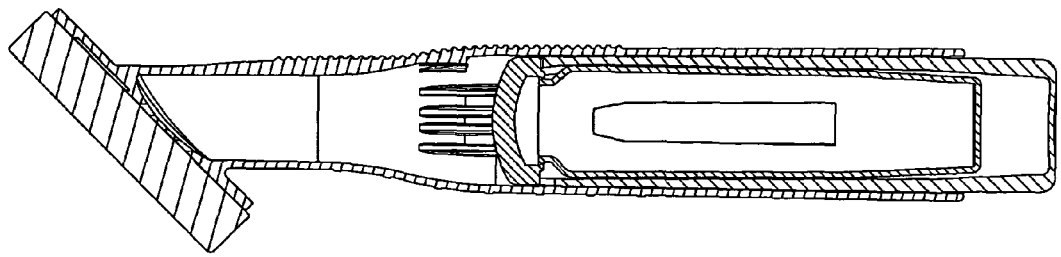
FIGS. 8A-8C illustrate cross-sectional side views of a system for applying a fluid, assembled with differently sized fluid containers.
Figure 8B:
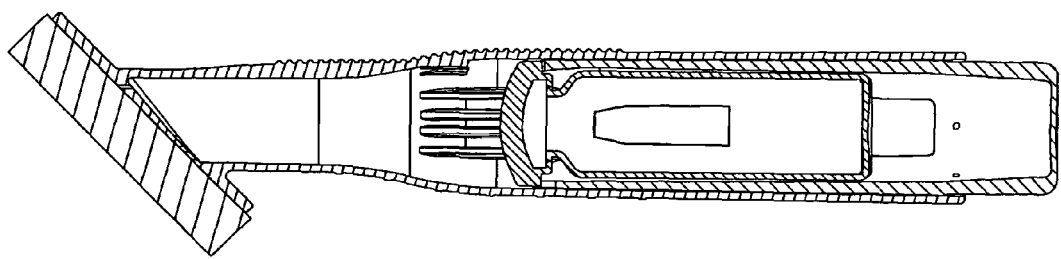
Figure 8C:
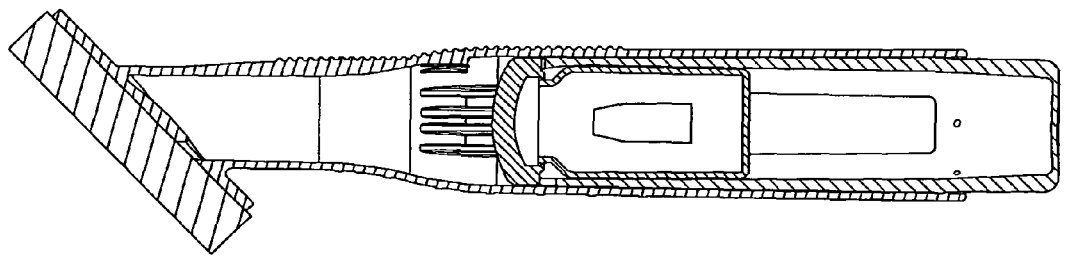

In some embodiments, system 10 may be configured to apply fluid from differently sized fluid containers. For example, as shown in FIGS. 8A-8C, because actuator sleeve 26 exerts force on container 12 at distal end 42 of container 12, applicator device 14 may be used with containers having a variety of lengths.

Figure 9:
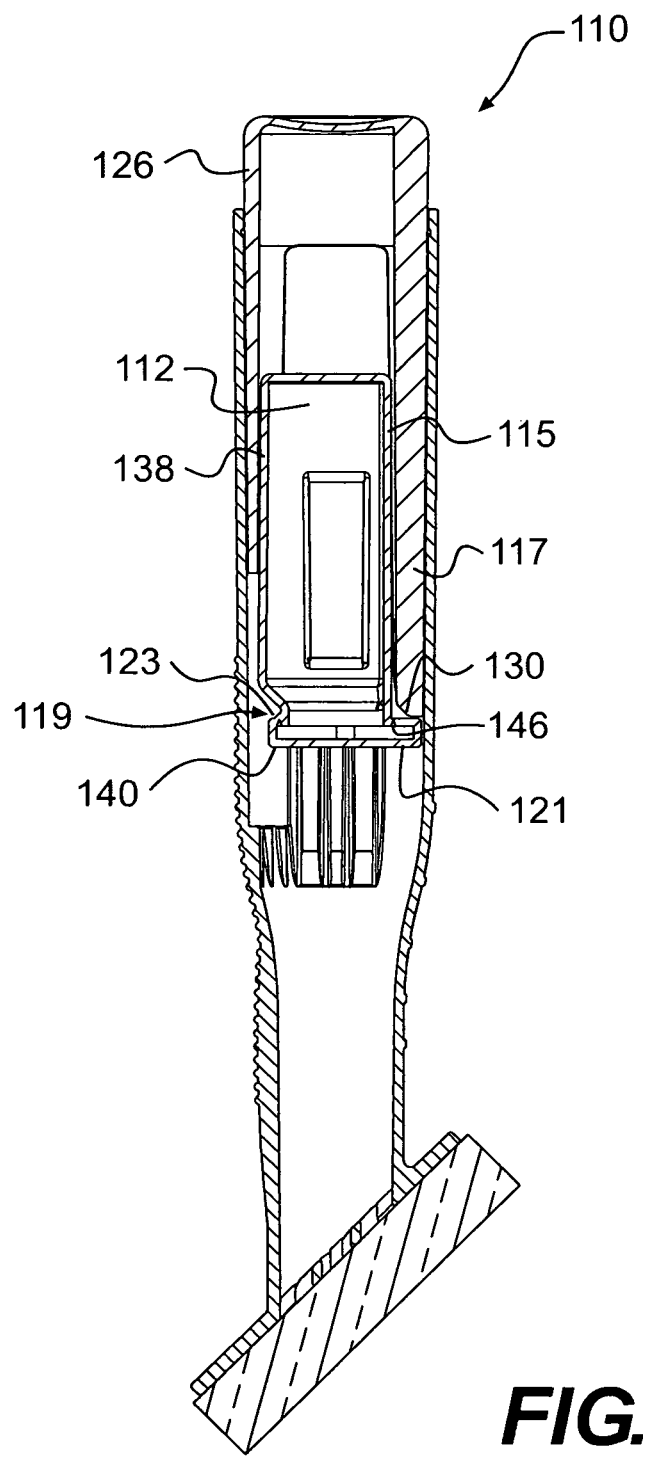
FIG. 9 is a cross-sectional view of an alternative embodiment of a system for applying a fluid.
Figure 10:
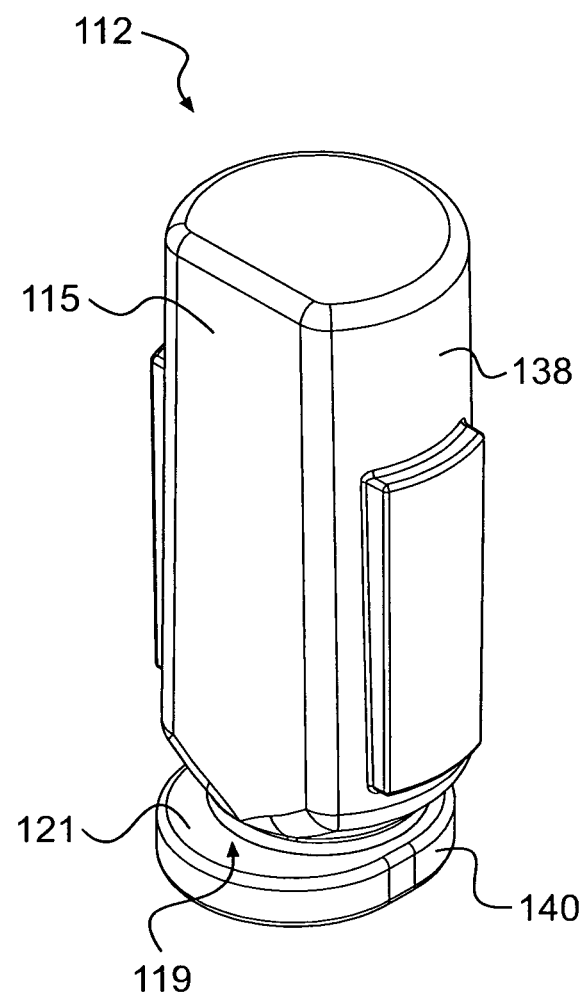
FIG. 10 is a container configured for use in the system shown in FIG. 9.

FIG. 9 is a cross-sectional view of a system 110 for applying a fluid, shown assembled and in a pre-actuated state. As shown in FIG. 9, system 110 may comprise a container 112 that may have a flat side 115. (See also, FIG. 10.) System 110 may include an actuator sleeve 126, having a thicker, and thus reinforced, portion 117, which corresponds with flat side 115 of container 112. For example, as shown in FIG. 9, thicker portion 117 of actuator sleeve 126 may abut flat side 115 of container 112 when system 110 is assembled. In other embodiments, container 12 and hollow body 16 in a similar but alternative way, for example, with corresponding tongue and groove, an inset protrusion, etc.

As shown in FIG. 9, container 112 may include a main body portion 138 and a cap portion 140. Container 112 may include a neck portion 119 between main body portion 138 and cap portion 140. Neck portion 119 may include a frangible portion 146. Frangible portion 146 may be configured to fracture as actuator sleeve 126 is longitudinally translated in a distal direction to act upon container 112 by forcing a distal end 130 of actuator sleeve 126 against cap portion 140 of container 112. Cap portion 140 may include a protruding element 121, which may be acted upon by distal end 130 of actuator sleeve 126.

In some embodiments, container 112 may include a hinge element 123 between main body portion 138 and cap portion 140. For example, container 112 may include frangible portion 146 on the side of container 112 where actuator sleeve 126 comes into contact with cap portion 140. Hinge element 123 may be disposed opposite frangible portion 146 so that upon longitudinal translation of actuator sleeve 126, frangible portion 146 fractures, separating cap portion 140 from main body portion 138, except at hinge element 119, which may maintain a connection between main body portion 138 and cap portion 140 of container 112, thus allowing cap portion 140 to flip open.

Figure 11A:
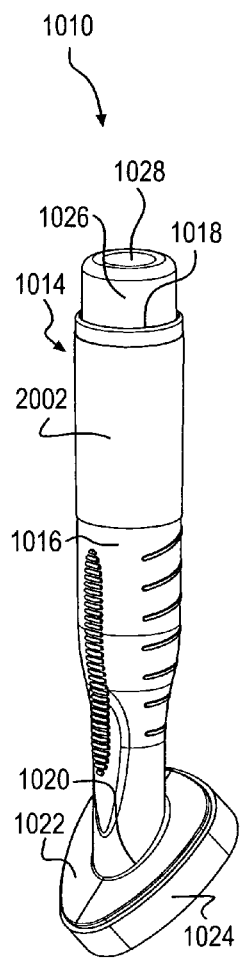
FIGS. 11A-11C illustrate perspective views of an another exemplary embodiment of an applicator system for applying a fluid in various stages of assembly.

FIGS. 11A-17B illustrate various alternative embodiments of the hollow body, container, and actuator sleeve, which may be combined as shown or with other embodiments, including those disclosed above, as will be understood by one skilled in the art. FIGS. 11A-11C illustrate a system 1010 in various stages of assembly. FIG. 11A shows system 1010 fully assembled. As shown in FIGS. 11B and 11C, system 1010 may include a container 1012 configured to contain a fluid. In addition, system 1010 may include an applicator device 1014 configured to apply a fluid to a surface. Applicator device 1014 may include a handle comprising an elongate hollow body 1016. Hollow body 1016 may also include a proximal end 1018 and a distal end 1020.

Hollow body 1016 may be configured to have container 1012 inserted therein. (See, e.g., FIG. 12A.) Applicator device 1014 may include a base 1022 at distal end 1020 of hollow body 1016 and an applicator pad 1024 coupled to base 1022. In addition, applicator device 1014 may include an annular actuator sleeve 1026 having a proximal end 1028 and a distal end 1030 and may be configured to be installed within hollow body 1016 between an inner surface 1032 (see, e.g., FIG. 12A) of an outer wall 1034 of hollow body 1016 and an outer wall 1036 of container 1012 such that actuation of actuator sleeve 1026 may release the fluid from container 1012, allowing the fluid to flow to applicator pad 1024.

Container

As shown in FIGS. 12A and 12B, container 1012 may include a main body portion 1038 and cap portion 1040 at a distal end 1042 of main body portion 1038. Container 1012 may be configured to be inserted into hollow body 1016 with distal end 1042 of container 1012 oriented toward distal end 1020 of hollow body 1016, as shown in FIG. 12A. In some embodiments, cap portion 1040 may be removable from main body portion 1038. For example, cap portion 1040 may be press-fit, snap-fit, threaded, etc. onto, or into, main body portion 1038. In certain embodiments, cap portion 1040 may be integrally formed with main body portion 1038.

In some embodiments, container 1012 may include a frangible portion 1046, as shown in FIG. 12B, between main body portion 1038 and cap portion 1040, wherein frangible portion 1046 is configured to break upon displacement of cap portion 1040 by actuator sleeve 1026. That is, in some embodiments, pushing cap portion 1040 off of container 1012, involves breaking container 1012 at frangible portion 1046. Once cap portion 1040 is removed from container 1012, the opening created at distal end 1042 of container 1012 may be of a size and shape that allows container 1012 to self-vent and drain. In certain embodiments, cap portion 1040 may be configured to be pushed off container 1012 in a longitudinal direction within hollow body 1016 upon the longitudinal translation of actuator sleeve 1026. In some embodiments container 1012 may be opened by puncturing a distal end of container 1012.

Figure 16A:
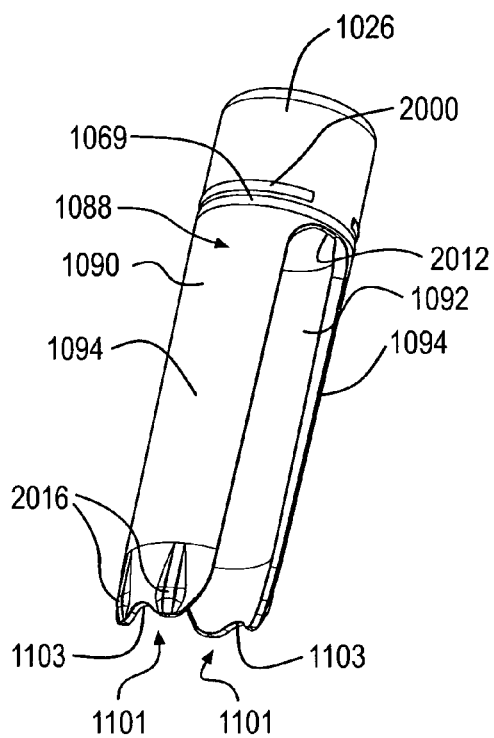
FIGS. 16A-16D illustrate several exemplary disclosed embodiments of actuator sleeves.
Figure 16B:
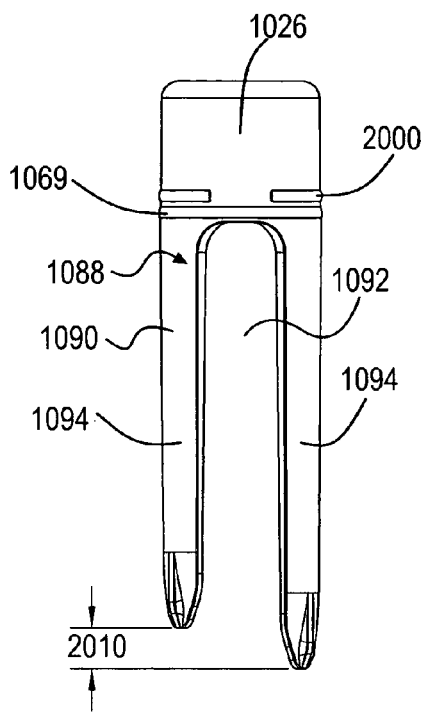
Figure 16C:
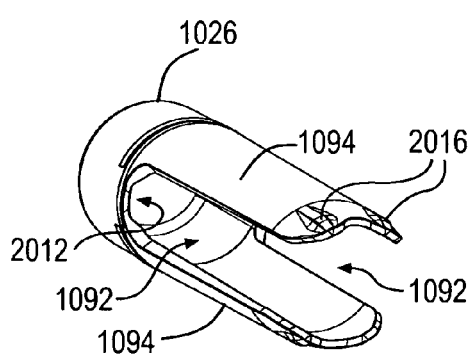
Figure 16D:
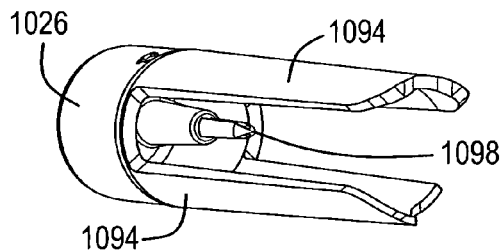
Figure 17A:
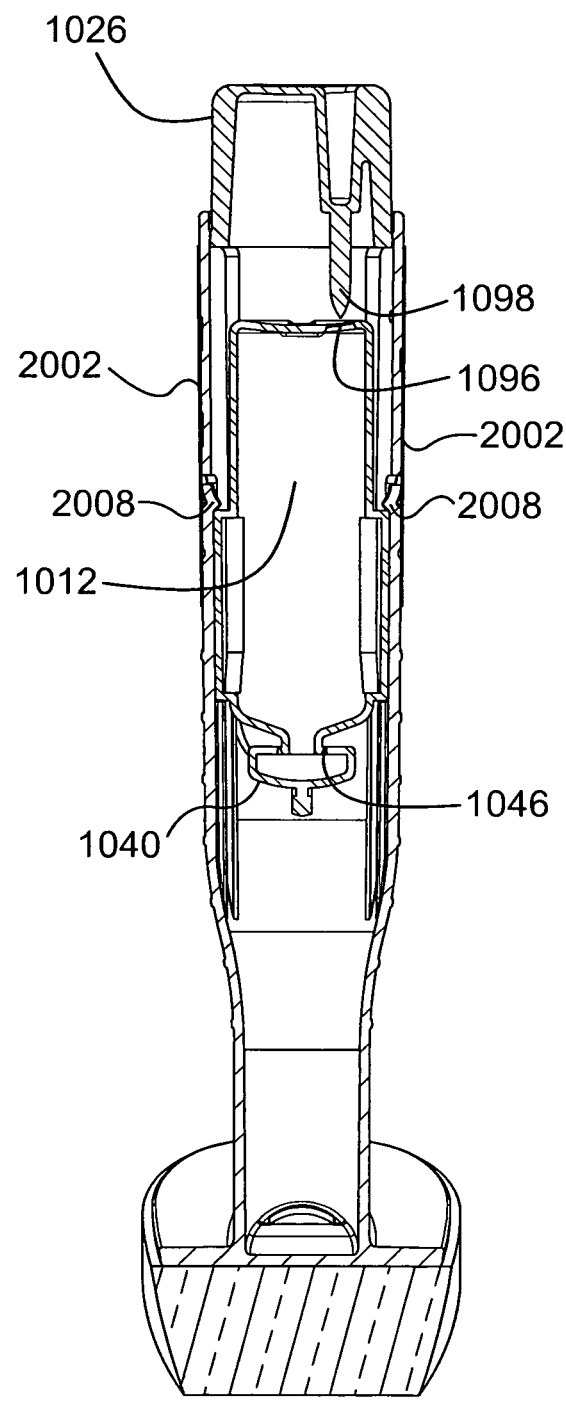
FIG. 17A illustrates a cross-sectional front view of a system for applying a fluid, according to an exemplary disclosed embodiment.
Figure 17B:
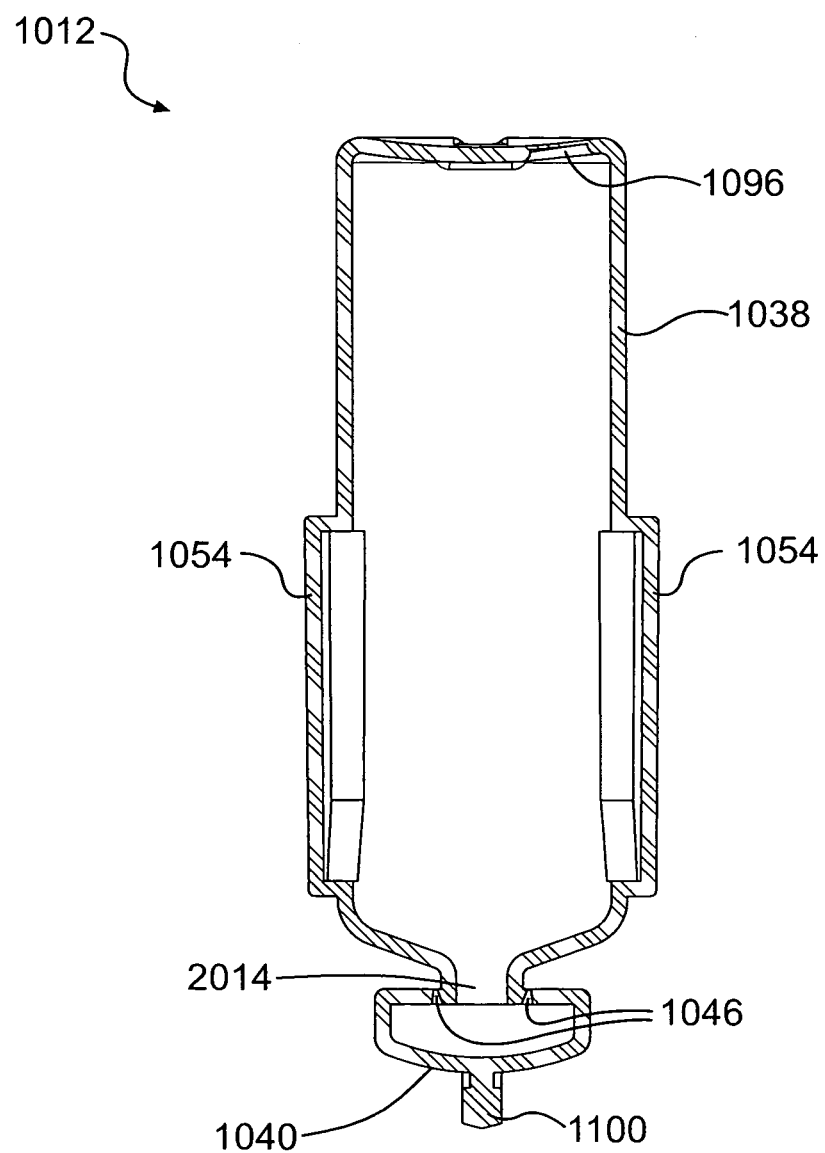
FIG. 17B illustrates a cross-sectional front view of a fluid container for use in the system shown in FIG. 17A.

In some embodiments, container 1012 may include a vent feature 1096, as shown in FIGS. 17A and 17B. Vent feature 1096 may be located at a proximal end of container 1012 and may include, for example, a thinner portion of material, readily puncturable by a corresponding puncturing element, such as a spike 1098, on actuator sleeve 1026, as shown in FIGS. 16D and 17A. Upon longitudinally translating actuator sleeve 1026, spike 1098 may puncture container 1012, allowing air to enter container 1012 to replace fluid as it drains from container 1012 once cap portion 1040 has been removed from container 1012. Such venting of container 1012 may facilitate more rapid and/or predictable flow of fluid out of container 1012.

Container 1012 may be formed of any type of material that is suitable for forming a fluid-holding container with a frangible or removable cap portion. Exemplary such materials are discussed above with respect to container 12.

The liquid contained in container 1012 may be an antiseptic solution containing an active ingredient. Exemplary such antiseptic solution active ingredients are discussed above.

In some embodiments of system 1010 applicator device 1014 may be provided in ready to use form. For example, applicator device 1014 may be stored, packaged, and/or shipped, etc. with applicator pad 1024 attached to base 1022 and with container 1012 and actuator sleeve 1026 inserted within hollow body 1016, as shown in FIG. 12A. In such embodiments, container 1012 may be pre-filled with a fluid, such as an antiseptic fluid, for example.

Container 1012 may include a neck portion 2014 as in FIG. 17B. In some embodiments, neck portion 2014 may be configured to facilitate metering of fluid flow. For example, neck portion 2014 may have a somewhat narrower size, thus restricting the flow rate of fluid out of container 1012.

As with system 10, in some embodiments, system 1010 may be configured to apply fluid from differently sized fluid containers. (See FIGS. 8A-8C.) In addition, system 1010 may also be configured to include a container having at least one flat side, similar to that shown in FIGS. 9 and 10.

Hollow Body

Figure 13A:
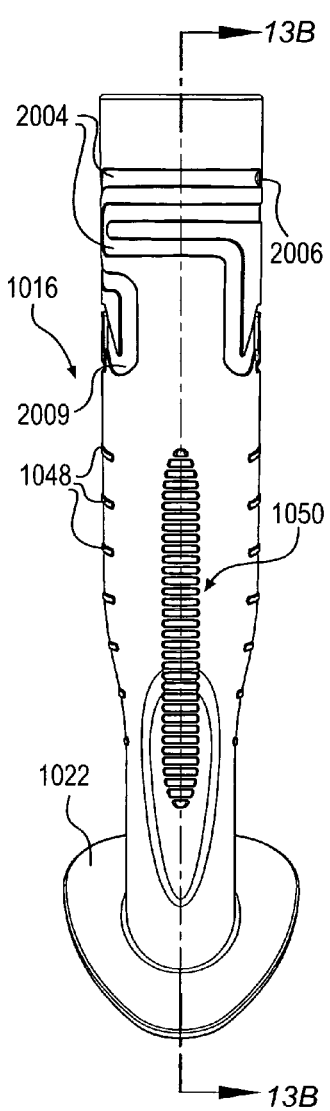
FIG. 13A illustrates a front view of a handle and base of a fluid applicator device, according an exemplary disclosed embodiment.

As illustrated by FIG. 13A, hollow body 1016 may include various shaping, sizing, and/or one or more exterior gripping features to facilitate manipulation of applicator device 1014 by a user. For example, hollow body 1016 may include indentations, protrusions, texture, rubberized material, etc., to promote secure gripping of hollow body 1016. For instance, as shown in FIG. 13A, hollow body 1016 may include one or more protruding gripping members 1048 and/or a textured gripping strip 1050. In some embodiments more than one textured gripping strip 1050 may be provided. Also, in some embodiments, hollow body 1016 may include an ergonomic bend (not shown) and/or a widened exterior portion configured to conform to contours of a hand palm.

Hollow body 1016 and/or base 1022 may be made of any suitable material. Exemplary materials are discussed above with respect to hollow body 16 and base 22. Hollow body 1016 may be made by various manufacturing processes known in the art including, but not limited to, molding, injection molding, machining, casting, extruding, and/or combinations thereof.

In some embodiments, one or more components of applicator 1012 may be formed of a transparent or translucent material. For example, one or more portions of hollow body 1016 and/or actuator sleeve 1026 may be formed of a transparent or translucent material. Transparency and/or translucency of certain components may enable observation of the quantity of fluid remaining in container 1012 and/or facilitate monitoring the flow of the fluid through applicator device 1014 while being dispensed.

Figure 13B:
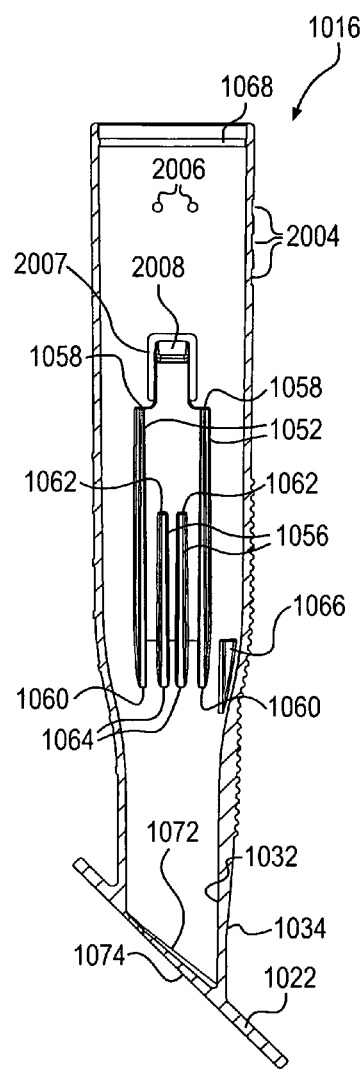
FIG. 13B illustrates a cross-sectional side view of the handle and base shown in FIG. 13A.
Figure 13C:
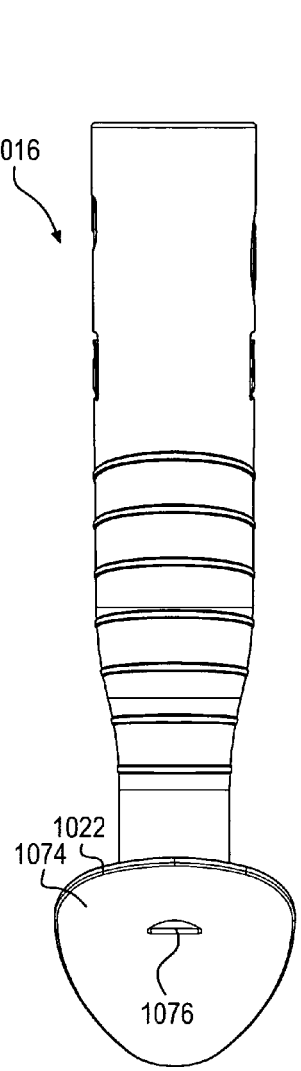
FIG. 13C illustrates a rear view of the handle and base shown in FIG. 13A.

Hollow body 1016 may include one or more interior guiding elements configured to orient and guide container 1012 when container 1012 is disposed within hollow body 1016. For example, as shown in FIG. 13B, hollow body 1016 may include one or more longitudinal, interior guiding ribs 1052 disposed on inner surface 1032 of hollow body 1016. Interior guiding ribs 1052 may be configured to restrict rotation of container 1012 within hollow body 1016. For example, in some embodiments, hollow body 1016 may include two substantially parallel guiding ribs 1052 spaced apart from one another. In such embodiments, container 1012 may include a corresponding outward protrusion 1054, as shown, for example, in FIG. 12A, having a size and shape to fit within, and be guided by, guiding ribs 1052. Alternatively, or additionally, hollow body 1016 may include one or more grooves (not shown) for orienting and guiding container 1012. For example, in certain embodiments, guiding ribs 1052 may, instead, be grooves in inner surface 1032 of hollow body 1016.

As also shown in FIG. 13B, hollow body 1016 may include one or more longitudinal stopping ribs 1056, substantially parallel to, and disposed between, guiding ribs 1052. Each of guiding ribs 1052 may include a proximal end 1058 and a distal end 1060 and each of stopping ribs 1056 may have a proximal end 1062 and a distal end 1064. In some embodiments, proximal end 1062 of each of stopping ribs 1056 may be located distal to the proximal ends 1058 of guiding ribs 1052 and may be configured to interact with a distal end 1065 (see FIG. 14A) of outward protrusion 1054 on container 1012 in order to stop longitudinal translation of container 1012 in a distal direction within hollow body 1016. Applicator device 1014 may be configured so that, when longitudinal translation of container 1012 in a distal direction is prevented by stopping ribs 1056 and rotational translation is prevented by guiding ribs 1052, longitudinal translation of actuator sleeve 1026 pushes container cap portion 1040 to remove cap portion 1040 from container 1012, as shown in FIG. 14A.

Figure 15A:
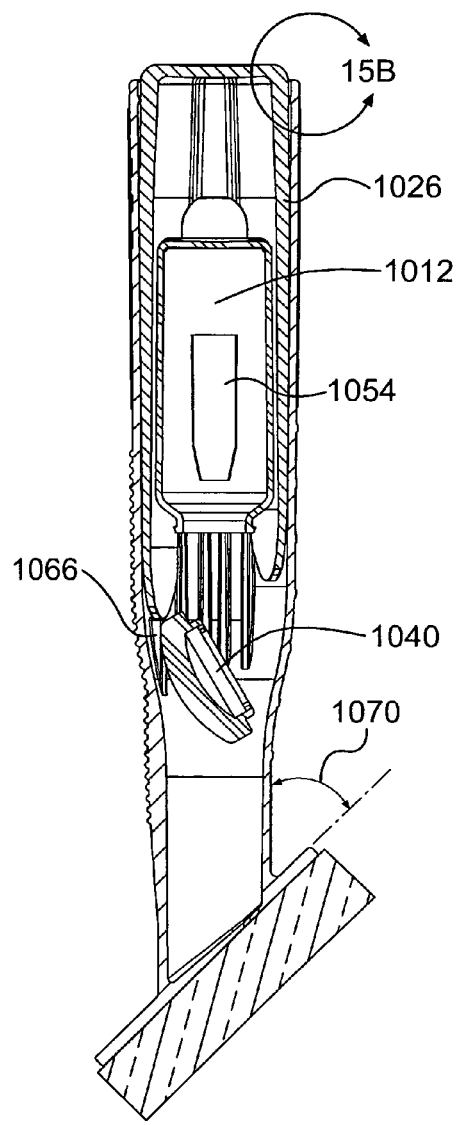
FIG. 15A illustrates a cross-sectional side view of an exemplary assembled applicator system in an activated state.

Hollow body 1016 may also include one or more inwardly projecting protrusion 1066. As shown in FIG. 15A, inwardly projecting protrusion 1066 may be further configured to reorient cap portion 1040 of container 1012 after being broken off of container 1012 by actuation of actuator sleeve 1026, for example, by tilting cap portion 1040 to prevent cap portion 1040 from becoming lodged within hollow body 1016, which could result in a blockage or reduction in flow of the fluid down to applicator pad 1024. As also shown in FIG. 15A, inwardly projecting protrusion 1066 may be configured to stop longitudinal translation of actuator sleeve 1026. That is, inwardly projecting protrusion 1066 may serve as a stop to define the limit of longitudinal translation of actuator sleeve 1026.

Figure 15B:
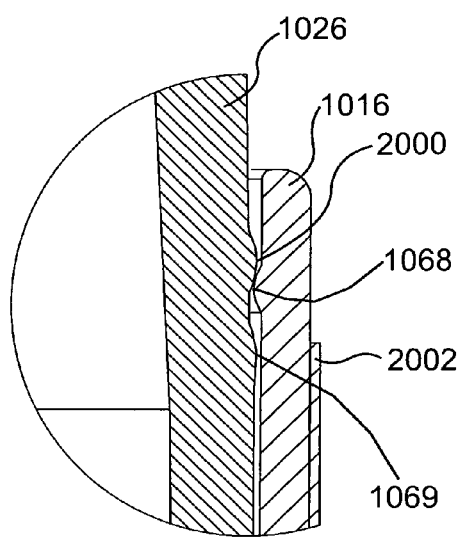
FIG. 15B illustrates a close-up view of a portion of the applicator system shown in FIG. 15B, showing sealing and retention features.

Hollow body 1016 may also include one or more interior restraining and/or sealing features at proximal end 1018 of hollow body 1016. For example, as shown in FIGS. 13B and 15B, in some embodiments, hollow body 1016 may include a circumferential restraining rib 1068 configured to secure actuator sleeve 1026 within hollow body 1016. Restraining rib 1068 may be configured to interact with corresponding features on actuator sleeve 1026. For example, as shown in FIGS. 11B and 15B, actuator sleeve 1026 may include a circumferential sealing rib 1069 configured to not only seal the interface between actuator sleeve 1026 and hollow body 1016 to prevent leakage, but also interact with restraining rib 1068, whereby restraining rib 1068 serves as a stop preventing actuator sleeve 1026 from being moved proximally beyond a point at which sealing rib 1069 contacts restraining rib 1068.

Restraining rib 1068 and sealing rib 1069 may have the same or different profile. Although the accompanying figures show a restraining rib 1068 on hollow body 1016 and a sealing rib on actuator sleeve 1026, in certain embodiments, the restraining rib and sealing rib could be reversed so that the sealing rib could be located on hollow body 1016 and the restraining rib could be located on actuator sleeve 1026. In addition, while the figures illustrate restraining and sealing features that include ribs, in some embodiments, the restraining and sealing features may include bosses, debosses, detents, etc. (Not shown.)

Figure 11B:
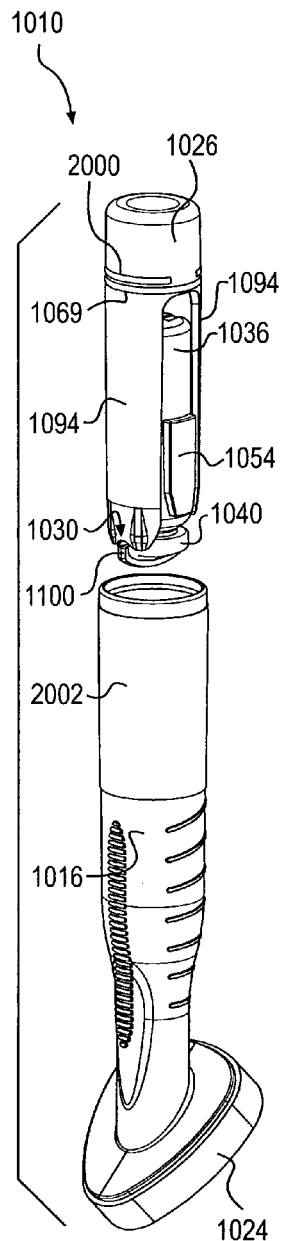
Figure 11C:
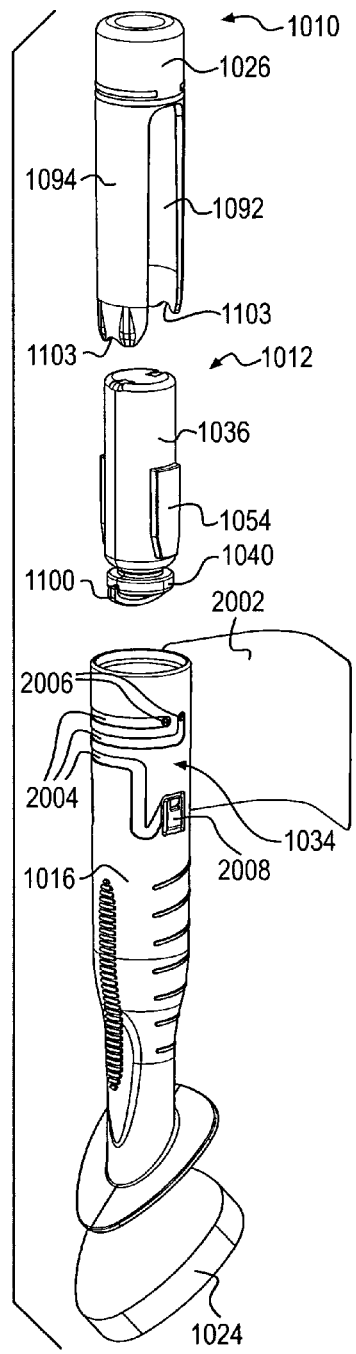

Applicator device 1014 may include a label 2002 configured to be affixed to outer wall 1034 of hollow body 1016, as shown, for example, in FIGS. 11A-C. In addition to providing a surface upon which information may be written/typed/etc., label 2002 may interact with one or more features of hollow body 1016. In some embodiments, label may be removable.

For example, in some embodiments, hollow body 1016 may include one or more venting channels 2004 in communication with one or more holes 2006 and one or more apertures 2007, each of which perforate outer wall 1034 of hollow body 1016. (See FIGS. 11C, 13A, and 13B.) When covered by label 2002, venting channels 2004 may form tortuous passages through which air may vent between one area inside hollow body 1016 to another when in an upright ("in-use") position (e.g., with the proximal end of applicator device 1014 held higher than the distal end of applicator device 1014), and inhibit outflow of fluid when applicator device 1014 is laid on a flat surface (i.e., with hollow body 1016 oriented substantially parallel to the ground) or held inverted (i.e., with applicator pad 2024 held higher than the proximal end of applicator device 1014). For example, channels 2004, holes 2006, and apertures 2007 may allow air to flow between a proximal area (in communication with holes 2006) and a more distal area (in communication with apertures 2007), when applicator device 1014 is held upright. This may promote self-draining of container 1012. In addition, the tortuous passages formed by channels 2004 may prevent leakage of fluid when applicator device is oriented horizontally or inverted. In order to prevent fluid leakage in an inverted orientation, one or more apertures 2007 may be located distally of the highest fluid level that would occur within hollow body 1016 once the fluid is released from container 1012. Alternatively, or additionally, channels 2004 may include a distally projecting loop 2009 that extends distal to the highest fluid level that could occur within hollow body 1016.

Label 2002 may be affixed to outer wall 1034 of hollow body 1016 via any suitable method. For example, label 2002 may be affixed to outer wall 1034 of hollow body 1016 via pressure sensitive adhesives, RF welding, heat staking, etc.

Also, in some embodiments, hollow body 1016 may include one or more container retention tabs 2008. Apertures 2007 may include a U-shaped opening about retention tabs 2008, as shown in FIGS. 11C and 13A. In some embodiments, retention tabs 2008 may be locked into place when label 2002 is affixed to outer wall 1034 of hollow body 1016 over retention tabs 2008. (See FIGS. 11C, 12B, and 17A.) As shown in FIG. 12B, retention tabs 2008, may protrude inwardly above the proximal end of outward protrusion 1054 of container 1012 once container 1012 is pushed far enough distally into hollow body 1016 in order to prevent container 1012 from translating proximally. In some embodiments, retention tabs 2008 may be flexible so that container 1012 may be removed from hollow body 1016. Application of label 2002 to outer wall 1034 of hollow body 1016, however, may lock retention tabs 2008 in an inwardly protruding position, thus preventing removal of container 1012 from hollow body 1016. In certain embodiments, retention tabs 2008 may be substantially inflexible. In such embodiments, for example, a container could be locked into position by rotating the container. thereby positioning lateral protrusions of the container under retention tabs 2008. In some embodiments, the rotation of the container upon insertion into hollow body 1016 could be performed automatically, for example, upon insertion of an actuator sleeve into hollow body 1016.

Although retention tabs 2008 are shown as tabs, other container retention features may be utilized, such as rings, embosses, or debosses that may be able to flex outwardly and/or inwardly to permit assembly (i.e., insertion of container 1012 into hollow body 1016).

Base

According to certain embodiments, hollow body 1016 and base 1022 may define an angle 1070, as shown, for example, in FIG. 15A. Although the accompanying figures illustrate embodiments wherein angle 1070 is approximately 45 degrees, hollow body 1016 and base 1022 may define any angle within the range of 0 to 180 degrees.

As shown in FIG. 13B, base 1022 may include an inner surface 1072 and an outer surface 1074 to which applicator pad 1024 is configured to be affixed. Similar to base 22 discussed above, and shown in FIGS. 4A through 4H, base 1022 may include one or more perforations 1076. (See also FIG. 13C.) Applicator pad 1024 may be configured to be attached to base 1022 over perforations 1076. Perforations 1076 may allow flow of the fluid from hollow body 1016 to applicator pad 1024.

In some embodiments, outer surface 1074 may include one or more channels, such as channels 78 shown in FIG. 4G. Also, in some embodiments, outer surface 1074 of base 1022 may be textured and/or may have other surface treatments, as is shown in the appended figures and discussed above with respect to outer surface 74 of base 22 in FIG. 4H.

According to certain embodiments, base 1022 may couple to hollow body 1016. Base 1022 may couple to hollow body 1016 in a variety of ways known in the mechanical arts, including, but not limited to, attachments by hinges, adhesives, mechanical interlocks, threaded portions, press-fits, friction-fits, interference fits, slide-fits, and/or combinations thereof. According to other embodiments, base 1022 may be integrally formed with hollow body 1016. An integral base/handle combination may be manufactured by various processes known in the art, including, but not limited to, molding, injection molding, casting, machining, or combinations thereof. In certain embodiments, applicator device 1040 may include an interchangeable attachment between hollow body 1016 and base 1022.

Base 1022 may be formed in a variety of shapes and sizes. The discussion above (and corresponding figures) regarding the shapes and sizes of base 22 and applicator pad 24 also apply to the shapes and sizes of base 1022 and applicator pad 1024.

Applicator Pad

The features of applicator pad 1024 are discussed above (and shown in the appended figures) with respect to applicator pad 24.

Actuator Sleeve

Actuator sleeve 1026 may be configured to be actuated to release the fluid to applicator pad 1024 from container 1012. FIGS. 16A-16D illustrate various exemplary embodiments of actuator sleeve 1026. Actuator sleeve 1026 may have an outer wall 1088 having an outer surface 1090. Actuator sleeve 1026 may be configured to be inserted within hollow body 1016 so that outer surface 1090 of outer wall 1088 of actuator sleeve 1026 is disposed within inner surface 1032 of outer wall 1034 of hollow body 1016. Actuator sleeve 1026 may be configured to be actuated to release the fluid to applicator pad 1024 from container 1012. Actuator sleeve 1026 may be configured to be longitudinally translated within hollow body 1016 in order to release the fluid from container 1012. Actuator sleeve 1026 may be longitudinally translated within hollow body 1016 by applying force to proximal end 1028 of actuator sleeve 1026. In some embodiments, proximal end 1028 of actuator sleeve 1026 may be contoured to provide substantially even force distribution across proximal end 1028. For example, in certain embodiments, proximal end 1028 of actuator sleeve 1026 may have a rounded, convex surface. (See proximal end 28 of actuator sleeve 26 shown in FIG. 6D.) Such a convex surface may distribute force across proximal end 1028, thereby reducing the pressure felt by a user. For example, a rounded convex surface may distribute the force across the palm of a user. In other embodiments, proximal end 1028 of actuator sleeve 1026 may have a concave surface, as shown in FIGS. 11A and 14A, to evenly distribute the force across, for example, the thumb or finger of a user.

In some embodiments, actuator sleeve 1026 may include one or more notches 1092 extending from distal end 1030 of actuator sleeve 1026 toward proximal end 1028 of actuator sleeve 1026. In such embodiments, container 1012 may include a restraining feature, such as outward protrusion 1054, to orient and position container 1012 within hollow body 1016. Such a restraining feature may be configured to fit within notch 1092 in actuator sleeve 1026.

In some embodiments, actuator sleeve 1026 may include one or more longitudinal projections 1094 projecting distally and configured to interact with cap portion 1040 of container 1012 to remove cap portion 1040 from container 1012 to release the fluid from container 1012. For example, as shown in FIG. 16C, actuator sleeve 1026 may include two longitudinal projections 1094, which may define two notches 1092. An actuator sleeve having two notches 1092 may be compatible with a container 1012 having two outward protrusions 1054. (See FIG. 17A.)

As shown in FIGS. 16A-16D, longitudinal projections 1094 may be of unequal length in some embodiments. (See length differential 2010 in FIG. 16B.) In such embodiments, actuation of actuator sleeve 1026, by longitudinal translation, may cause cap portion 1040 to be pushed off of container 1012 one side at a time. For example, cap portion 1040 may include protruding elements 1100 (see FIG. 11C), which may interact with longitudinal projections 1094 of actuator sleeve 1026 to remove cap portion 1040 from container 1012, thereby releasing the fluid from container 1012.

In some embodiments, longitudinal projections 1094 may include distal ends 1101 that may be configured to push protruding elements 1100 distally when actuator sleeve 1026 is longitudinally translated in the distal direction. As shown in FIG. 16A, in some embodiments, distal end 1101 of one or more longitudinal projections 1094 may include a recess 1103, which may be configured to interact with cap portion 1040 (e.g., with protruding element 1100; see FIG. 11B) to prevent rotation of cap portion 1040 during longitudinal translation of actuator sleeve 1026. In addition, each recess 1103 may function as a cradle to retain a corresponding protruding element 1100 of cap portion 1040 while distal end 1101 of longitudinal projections 1094 pushes cap portion 1040 off of container 1012 longitudinally.

Components of applicator system 1010, including applicator device 1014 and/or container 1012, may be configured to be sterilized in various ways known in the art including, but not limited to, exposure to ethylene oxide ("(Et)2O"), gamma radiation, electron beam, and/or steam. Additional information regarding sterilization is discussed above.

In addition to sealing rib 1069, actuator sleeve 1026 may also include a restraining feature, such as a rib or partial rib 2000. Partial rib 2000 may provide restraint of actuator sleeve 1026 to prevent unintended longitudinal translation of actuator sleeve 1026, e.g., during shipping/transport. For example, during shipping, restraining rib 1068 of hollow body 1016 may reside between sealing rib 1069 and partial rib 2000 of actuator sleeve 1026. Although the appended figures illustrate restraining and sealing features (e.g., partial rib 2000) that include ribs, in some embodiments, the restraining and sealing features may include bosses, debosses, detents, etc. (Not shown.)

In some embodiments, actuator sleeve 1026 may also include one or more flow features, such as cutouts 2012, as shown in FIGS. 16A and 16C. Cutouts 2012 may allow fluid to flow freely around the exterior of container 1012 to reduce the potential for fluid becoming trapped between container 1012 and the proximal interior of actuator sleeve 1026 following device actuation.

In addition, longitudinal projections 1094 may include one or more knobs 2016 at the distal end. Knobs 2016 may prevent radially outward deflection of the distal ends of longitudinal projections 1094 during actuation. This ensures that longitudinal projections 1094 do not miss cap portion 1040 of container 1012. In addition, knobs 2016 may provide reinforcement to the distal tips of longitudinal projections 1094.

As discussed above, spike 1098 may be included on actuator sleeve 1026 for puncturing a proximal end of container 1012.

Various other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An applicator device for applying a fluid comprising:
   an elongate hollow body having a proximal end and a distal end;
   an applicator pad disposed at the distal end of the hollow body; and
   an actuator sleeve to be inserted within the hollow body, the actuator sleeve including at least one longitudinal projection that distally projects;
   wherein when the actuator sleeve is distally translated within the hollow body, the at least one longitudinal projection contacts against a distally-located cap portion of a fluid containing container, to open the cap portion distally from a main body portion of the fluid containing container, thus releasing the liquid from the container to the applicator pad;
   wherein the fluid containing container has radially protruding elements on the cap portion and outward protrusions on the main body portion, the outward protrusions being circumferentially separated and extending radially outward to create a discontinuous outer diameter of the fluid containing container;
   wherein the outward protrusions are located proximally to a frangible or separable portion of the fluid containing container and the radially protruding elements are located distally to the frangible or separable portion; and
   wherein the fluid containing container is located within the hollow body by fitting the outward protrusions to respective ribs disposed on an inner surface of the elongate hollow body such that the fluid containing container is inhibited from being distally and circumferentially translated.

2. The applicator device of claim 1, wherein the radially protruding elements protrude toward an inner wall of the hollow body, and the at least one longitudinal projection of the actuator sleeve acts upon at least one radially protruding element, thus opening the cap portion.

3. The applicator device of claim 2, wherein the at least one longitudinal projection of the actuator sleeve distally pushes the at least one radially protruding element of the cap portion, thus opening the cap portion.

4. The applicator device of claim 3, wherein the actuator sleeve includes two longitudinal projections of unequal length so that, upon longitudinal translation of the actuator sleeve, each of the longitudinal projections pushes the cap portion off of the container.

5. The applicator device of claim 4, wherein at least one of the longitudinal projection has a recess that interacts with one of the radially protruding elements of the cap portion.

6. The applicator device of claim 3, wherein the actuator sleeve includes two longitudinal projections of equal length so that, upon longitudinal translation of the actuator sleeve, each of the longitudinal projections pushes the cap portion off of the container.

7. The applicator device of claim 6, wherein at least one of the longitudinal projections has a recess that interacts with one of the radially protruding elements of the cap portion.

8. The applicator device of claim 2, wherein the actuator sleeve includes two longitudinal projections of unequal length so that a tip of a longer one of the longitudinal projections interacts with one of the radially protruding elements.

9. The applicator device of claim 2, wherein the actuator sleeve includes two longitudinal projections of unequal length so that a longer one of the longitudinal projections of the actuator sleeve includes an inwardly projecting longitudinal rib, the longitudinal rib interacting with one radially protruding element.

10. The applicator device of any one of claims 2 to 9, wherein the main body portion of the fluid containing container and the cap portion are formed integrally with each other via a neck portion having the frangible or separable portion, the frangible or separable portion being broken or separated when the longitudinal projection of the actuator sleeve pushes the at least one radially protruding element of the cap portion.

11. The applicator device of claim 10, wherein the frangible or separable portion is formed at the entire circumference of the neck portion.

12. The applicator device of claim 10, wherein the frangible or separable portion is formed at a part of the neck portion.

13. The applicator device of claim 10, wherein the fluid containing container includes a hinge element which is located opposite to the frangible or separable portion and is configured to maintain a connection between the main body portion and the cap portion after the frangible or separable portion breaks or separates, thus allowing the cap portion to flip open.

14. The applicator device of claim 2, wherein the at least one longitudinal projection of the actuator sleeve exerts a circumferential force on at least one of the radially protruding elements of the cap portion to cause the cap portion to rotate, thus breaking or separating the frangible or separable portion and opening the cap portion.

15. The applicator device of claim 14, wherein the at least one longitudinal projection of the actuator sleeve has an angled surface, the angled surface acting upon at least one of the radially protruding elements, thus rotating the cap portion.

16. The applicator device of claim 14, wherein the actuator sleeve includes two longitudinal projections, one of the longitudinal projections having an angled surface whereas the other longitudinal projection has a tooth for interacting with at least one of the radially protruding elements of the cap portion to prevent counter-rotation of the cap portion.

17. The applicator device of claim 1, wherein the hollow body includes one or more interior restraining features at the proximal end of the hollow body, including one or more ribs, bosses, or detents configured to secure the actuator sleeve within the hollow body.

18. The applicator device of claim 17, wherein the ribs include at least one longitudinal, interior guiding rib located on an inner surface of an outer wall of the hollow body and configured to orient and guide the container when the container is located within the hollow body.

19. The applicator device of claim 18, wherein the at least one longitudinal, interior guiding rib includes two parallel guiding ribs spaced apart from one another; and
wherein the outward protrusions of the container are configured to fit within, and be guided by, the spaced apart, parallel guiding ribs.

20. The applicator device of claim 19, wherein the hollow body further includes one or more longitudinal stopping ribs, parallel to and disposed between the guiding ribs; and
wherein each of the guiding ribs has a proximal end and a distal end and each of the stopping ribs has a proximal end and a distal end, the proximal end of each of the stopping ribs being located distal to the proximal ends of the guiding ribs and being configured to interact with respective distal ends of the outward protrusions of the container in order to stop longitudinal translation of the container in a distal direction within the hollow body.

21. The applicator device of claim 17, wherein the hollow body includes one or more container retention tabs; and
wherein once the container is pushed distally into the hollow body, the retention tabs protrude inwardly above a proximal end of the container, in order to prevent the container from translating proximally.

22. The applicator device of claim 1, wherein the hollow body includes an inwardly projecting protrusion configured to stop longitudinal translation of the actuator sleeve; and
wherein the inwardly projecting protrusion is configured to reorient the cap portion of the container after being broken off of the container by actuation of the actuator sleeve.

23. The applicator device of claim 1, wherein the proximal end of the actuator sleeve includes a sealing feature configured to interact with an inner surface of an outer wall of the hollow body to prevent leakage of the fluid from the hollow body.

24. The applicator device of claim 1, wherein the actuator sleeve includes a partial rib disposed circumferentially about a proximal end of the actuator sleeve; and
wherein the partial rib is configured to interact with a corresponding restraining rib on an inner surface of the hollow body.

25. The applicator device of claim 1, wherein the actuator sleeve includes at least one notch extending from a distal end of the actuator sleeve toward a proximal end of the actuator sleeve; and
wherein at least one of the outward protrusions of the container is configured to fit within the at least one notch in the actuator sleeve.

26. The applicator device of claim 1, wherein the at least one longitudinal projection includes one or more features at a distal end to prevent radially outward deflection of the distal end of the at least one longitudinal projection during actuation.

27. The applicator device of claim 1, wherein the actuator sleeve has a proximal end and a distal end and is configured to be installed between an inner surface of an outer wall of the hollow body and an outer wall of the container, longitudinal translation of the actuator sleeve within the hollow body releasing the fluid from the container, thus allowing the fluid to flow to the applicator pad;
wherein the container includes a flat side; and
wherein the actuator sleeve includes a thicker, reinforced portion, which corresponds with the flat side of the container.

28. The applicator device of claim 1, further comprising a label configured to be affixed to an outer wall of the hollow body, wherein when covered by the label, venting channels form one or more tortuous passages, through which air may vent to and/or from inside the hollow body when in an upright, in-use position, and inhibit outflow of fluid when the applicator device is laid on a flat surface with the hollow body oriented parallel to the ground.

29. An applicator system for applying a fluid comprising:
an applicator device including:
an elongate hollow body having a proximal end and a distal end;
an applicator pad disposed at the distal end of the hollow body; and
an actuator sleeve to be inserted within the hollow body, the actuator sleeve including at least one longitudinal projection that distally projects; and
a fluid containing container located within the hollow body such that a cap portion is distally located, the fluid containing container having radially protruding elements on the cap portion and outward protrusions on a main body portion, the outward protrusions being circumferentially separated and extending radially outward to create a discontinuous outer diameter of the fluid containing container;

wherein the outward protrusions are located proximally to a frangible or separable portions of the fluid containing container and the radially protruding elements are located distally to the frangible or separable portion;

wherein the fluid containing container is located within the hollow body by fitting the outward protrusions to respective ribs disposed on an inner surface of the elongate hollow body such that the fluid containing container is inhibited from being distally and circumferentially translated; and wherein when the actuator sleeve is distally translated within the hollow body, the at least one longitudinal projection contacts against the distally-located cap portion of the fluid containing container, to open the cap portion distally from the main body portion of the fluid containing container, thus releasing the liquid from the container to the applicator pad.

30. The applicator system of claim 29, wherein the at least one longitudinal projection of the actuator sleeve distally pushes at least one of the radially protruding elements of the cap portion, thus opening the cap portion.

31. The applicator system of claim 30, wherein the actuator sleeve includes two longitudinal projections of unequal length so that, upon longitudinal translation of the actuator sleeve, each of the longitudinal projections pushes the cap portion off of the container.

32. The applicator system of claim 30, wherein the actuator sleeve includes two longitudinal projections of equal length so that, upon longitudinal translation of the actuator sleeve, each of the longitudinal projections pushes the cap portion off of the container.

33. The applicator system of claim 30, wherein the actuator sleeve includes two longitudinal projections of unequal length so that a tip of a longer one of the longitudinal projections interacts with one of the radially protruding elements.

34. The applicator system of claim 30, wherein the actuator sleeve includes two longitudinal projections of unequal length so that a longer one of the longitudinal projections of the actuator sleeve includes an inwardly projecting longitudinal rib, the longitudinal rib interacts with one of the radially protruding elements.

35. The applicator system of claim 29, wherein the at least one longitudinal projection of the actuator sleeve exerts a circumferential force on at least one of the radially protruding elements of the cap portion to cause the cap portion to rotate, thus breaking or separating the frangible or separable portion and opening the cap portion.

36. The applicator system of claim 35, wherein the at least one longitudinal projection of the actuator sleeve has an angled surface, the angled surface acting upon at least one of the radially protruding elements, thus rotating the cap portion.

37. The applicator system of claim 35, wherein the actuator sleeve includes two longitudinal projections, one of the longitudinal projections having an angled surface whereas the other longitudinal projection has a tooth for interacting with at least one of the radially protruding elements of the cap portion to prevent counter-rotation of the cap portion.

38. A fluid containing container disposed in an applicator device for applying a fluid, the applicator device including:
an elongate hollow body having a proximal end and a distal end;
an applicator pad disposed at the distal end of the hollow body; and
an actuator sleeve to be inserted within the hollow body, the actuator sleeve including at least one longitudinal projection that distally projects;

wherein the fluid containing container has outward protrusions at a main body portion of the fluid containing container, and is located within the hollow body by fitting the outward protrusions to respective ribs disposed on an inner surface of the elongate hollow body such that a cap portion is distally located, and further, the container is inhibited from being distally and circumferentially translated;

wherein the outward protrusions are circumferentially separated and extend radially outward to create a discontinuous outer diameter of the fluid containing container;

wherein the fluid containing container has radially protruding elements on the cap portion, and is configured such that when the actuator sleeve is distally translated within the hollow body, the at least one longitudinal projection contacts against the radially protruding elements of the cap portion, to open the distally-located cap portion distally from the main body portion of the fluid containing container, thus releasing the fluid to the applicator pad; and wherein the outward protrusions are located proximally to a frangible or separable portion of the fluid containing container and the radially protruding elements are located distally to the frangible or separable portion.

39. The fluid containing container of claim 38, further comprising a vent feature located at a proximal end of the container.

40. The fluid containing container of claim 39, wherein the vent feature includes a thin portion of material, which is readily puncturable by a corresponding puncturing element on the actuator sleeve upon longitudinally translating the actuator sleeve.

41. The fluid containing container of claim 40, wherein the puncturing element includes a spike.

42. The fluid containing container of claim 38 comprising:
a neck portion between the main body portion and the cap portion,
the neck portion including:
the frangible or separable portion; and
a hinge element disposed opposite to the frangible or separable portion and configured to maintain a connection between the main body portion and the cap portion after the frangible or separable portion fractures or separates, thus allowing the cap portion to flip open.

43. The fluid containing container of claim 38, wherein the fluid containing container is formed into a blow-fill-seal container provided with the cap portion.

* * * * *

UNITED STATES PATENT AND TRADEMARK OFFICE
CERTIFICATE OF CORRECTION

| | |
|---|---|
| PATENT NO. | : 8,979,785 B2 |
| APPLICATION NO. | : 12/654664 |
| DATED | : March 17, 2015 |
| INVENTOR(S) | : Todd M. Korogi et al. |

It is certified that error appears in the above-identified patent and that said Letters Patent is hereby corrected as shown below:

In the Claims

Claim 5, column 20, line 48, "the longitudinal projection" should read -- the longitudinal projections --.

Signed and Sealed this
Seventh Day of July, 2015

Michelle K. Lee
*Director of the United States Patent and Trademark Office*